(12) United States Patent
Hunt et al.

(10) Patent No.: US 10,402,741 B2
(45) Date of Patent: Sep. 3, 2019

(54) ANALYTIC SYSTEM BASED ON MULTIPLE TASK LEARNING WITH INCOMPLETE DATA

(71) Applicant: SAS Institute Inc., Cary, NC (US)

(72) Inventors: Xin Jiang Hunt, Cary, NC (US); Saba Emrani, Santa Clara, CA (US); Jorge Manuel Gomes da Silva, Durham, NC (US); Ilknur Kaynar Kabul, Apex, NC (US)

(73) Assignee: SAS INSTITUTE INC., Cary, NC (US)

( * ) Notice: Subject to any disclaimer, the term of this patent is extended or adjusted under 35 U.S.C. 154(b) by 0 days.

(21) Appl. No.: 15/833,641

(22) Filed: Dec. 6, 2017

(65) Prior Publication Data

US 2018/0336484 A1    Nov. 22, 2018

Related U.S. Application Data

(60) Provisional application No. 62/508,357, filed on May 18, 2017.

(51) Int. Cl.
| | | |
|---|---|---|
| *G06N 7/00* | (2006.01) | |
| *G06F 17/16* | (2006.01) | |
| *G06F 17/18* | (2006.01) | |
| *G06N 20/00* | (2019.01) | |
| *G16H 10/00* | (2018.01) | |

(52) U.S. Cl.
CPC ............. *G06N 7/005* (2013.01); *G06F 17/16* (2013.01); *G06F 17/18* (2013.01); *G06N 20/00* (2019.01); *G16H 10/00* (2018.01)

(58) Field of Classification Search
CPC ............................ G06N 7/005; G06N 99/005
See application file for complete search history.

(56) References Cited

U.S. PATENT DOCUMENTS

2017/0124469 A1\*  5/2017  Hu .......................... G06F 19/12

OTHER PUBLICATIONS

Loh, P. L., & Wainwright, M. J. (2011). High-dimensional regression with noisy and missing data: Provable guarantees with non-convexity. In Advances in Neural Information Processing Systems (pp. 2726-2734). (Year: 2011).\*

(Continued)

*Primary Examiner* — Alexey Shmatov
*Assistant Examiner* — Oluwatosin O Alabi
(74) *Attorney, Agent, or Firm* — Bell & Manning, LLC

(57) ABSTRACT

A computing device computes a weight matrix to predict a value for a characteristic in a scoring dataset. For each of a plurality of related tasks, an augmented observation matrix, a plug-in autocovariance matrix, and a plug-in covariance vector are computed. A weight matrix used to predict the characteristic for each of a plurality of variables and each of a plurality of related tasks is computed. (a) and (b) are repeated with the computed updated weight matrix as the computed weight matrix until a convergence criterion is satisfied: (a) a gradient descent matrix is computed using the computed plug-in autocovariance matrix, the computed plug-in covariance vector, the computed weight matrix, and a predefined relationship matrix, wherein the predefined relationship matrix defines a relationship between the plurality of related tasks, and (b) an updated weight matrix is computed using the computed gradient descent matrix.

30 Claims, 9 Drawing Sheets

(56) References Cited

OTHER PUBLICATIONS

Widmer, C., Kloft, M., Gömitz, N., & Rätsch, G. (Sep. 2012). Efficient training of graph-regularized Multitask SVMs. In Joint European Conference on Machine Learning and Knowledge Discovery in Databases (pp. 633-647). Springer, Berlin, Heidelberg. (Year: 2012).*
Bakker, B., & Heskes, T. (2003). Task clustering and gating for bayesian multitask learning. Journal of Machine Learning Research, 4(May), 83-99. (Year: 2003).*
Wu, Z., Jiang, Y. G., Wang, J., Pu, J., & Xue, X. (Nov. 2014). Exploring inter-feature and inter-class relationships with deep neural networks for video classification. In Proceedings of the 22nd ACM international conference on Multimedia (pp. 167-176). ACM. (Year: 2014).*
Jansen et al., Analyzing Incomplete Discrete Longitudinal Clinical Trial Data, Statistical Science, vol. 21, No. 1, 2006, pp. 52-69.
Widmer et al., Efficient Training of Graph-Regularized Multitask SVMs, Proceedings of the 2012 European conference on Machine Learning and Knowledge Discovery in Databases , Sep. 24, 2012.
T. Heskes, Empirical Bayes for Learning to Learn, 2000.
Candes et al., Exact Matrix Completion via Convex Optimization, May 2008.
Chen et al., Graph-Structured Multi-task Regression and an Efficient Optimization Method for General Fused Lasso Manuscript, arXiv:1005.3579v1, May 2010.
Loh et al., High-dimensional regression with noisy and missing data: Provable guarantees with non-convexity, Annals of Statistics, vol. 40, No. 3, 2012.
D. Rubin, Inference and Missing Data, Biometrika, vol. 63, Issue 3, Dec. 1976, pp. 581-592.
Obozinski et al., Joint covariate selection and joint subspace selection for multiple classification problems, Statistics and Computing, 20(2), Jan. 14, 2009, pp. 231-252.
Parameswaran et al., Large Margin Multi-Task Metric Learning, neural information processing systems, 2010.
Evgeniou et al., Learning Multiple Tasks with Kernel Methods, Journal of Machine Learning Research 6, Apr. 2005, pp. 615-637.
Cook et al., Marginal Analysis of Incomplete Longitudinal Binary Data: A Cautionary Note on LOCF Imputation, Biometrics 60, Sep. 2004, pp. 820-828.
Keshavan et al., Matrix Completion from a Few Entries, arXiv:0901.3150v4, Sep. 17, 2009.
Schafer et al., Missing Data: Our View of the State of the Art, Psychological Methods, vol. 7, No. 2, 2002, pp. 147-177.
Wang et al., Missing value estimation for DNA microarray gene expression data by Support Vector Regression imputation and orthogonal coding scheme, BMC Bioinformatics 7:32, Jan. 22, 2006.
Xue et al., Multi-Task Learning for Classification with Dirichlet Process Priors, Journal of Machine Learning Research 8, Jan. 2007, pp. 35-63.
Widmer et al., Multitask Learning in Computational Biology, JMLR: Workshop and Conference Proceedings 27, 2012, pp. 207-216.
Zhou et al., MALSAR: Multi-Task Learning Via Structural Regularization, User's Manual, Version 1.1, Dec. 18, 2012.
Quadrianto et al., Multitask Learning without Label Correspondences, Neural Information Processing Systems, Jan. 1, 2010.
R. Caruana, Multitask Learning, Machine Learning, 28, 1997, pp. 41-75.
Evgeniou et al., Regularized Multi-Task Learning, knowledge discovery and data mining, Aug. 22, 2004.
Bakker et al., Task Clustering and Gating for Bayesian Multitask Learning, Journal of Machine Learning Research 4, May 2003, pp. 83-99.
Tibshirani et al., The Solution Path of the Generalized Lasso, Annals of Statistics, vol. 39, issue 3, Jan. 6, 2011.
Loh et al., High-dimensional regression with noisy and missing data: Provable guarantees with non-convexity, neural information processing systems, 2011.
Wang et al., Multi-Task Classification for Incomplete Data, 2010.

* cited by examiner

ANALYTIC SYSTEM BASED ON MULTIPLE TASK LEARNING WITH INCOMPLETE DATA

CROSS-REFERENCE TO RELATED APPLICATIONS

The present application claims the benefit of 35 U.S.C. § 119(e) to U.S. Provisional Patent Application No. 62/508,357 filed on May 18, 2017, the entire contents of which are hereby incorporated by reference.

BACKGROUND

Multi-task learning is a type of transfer learning that trains multiple tasks simultaneously and leverages the shared information between related tasks to improve the generalization performance. Since different tasks may have different numbers of observations, missing target values can be handled in multi-task learning. Missing features in the input matrix used to predict the target value, however, need to be addressed.

Missing features (incomplete data) occur for different reasons in a wide variety of applications. For example, in clinical studies, some patients fail to answer some questions, or measurements of some biospecimens are partially lost at various stages. In bioinformatics, experimentation errors, image corruption, and damage to a slide cause missing gene expression samples. In image processing, objects may be partially obstructed from view result in incomplete observations. Moreover, malfunctioning or unreliable sensors in sensor networks may result in missing data.

Using some machine learning techniques, each observation with a missing feature may be deleted entirely. For small datasets, deleting observations may result in a dataset that is statistically non-representative or biased or result in considerable error in the trained model. As another option, instead of deleting the observation vector, a zero or other constant value possibly specified by a user may be used to provide the missing feature value. In some machine learning techniques, a value may be imputed for each missing feature before applying machine learning. For example, a mean value computed for the feature may be used to provide the missing feature value. As another option, a feature value from a most recent observation may be used to provide the missing feature value. As still another option, a matrix completion method may be used to provide the missing feature value. Imputation methods may neglect an uncertainty of missing values by replacing them with fixed instances, inducing bias and underrating data variability. Imputation methods further may be based on assumptions that are not valid in many cases.

SUMMARY

In an example embodiment, a non-transitory computer-readable medium is provided having stored thereon computer-readable instructions that, when executed by a computing device, cause the computing device to compute an updated weight matrix used to predict a value for a characteristic in a scoring dataset. For each of a plurality of related tasks, an augmented observation matrix is computed, a plug-in autocovariance matrix is computed using the computed augmented observation matrix and a noise value, and a plug-in covariance vector is computed. The augmented observation matrix is computed using an observation matrix and a predefined probability value that a value is missing in the observation matrix. The observation matrix includes a plurality of observation vectors. Each observation vector includes a plurality of values. Each value of the plurality of values is associated with a variable to define a plurality of variables. The plug-in covariance vector is computed using a target vector, the computed augmented observation matrix, and the noise value. The target vector includes a target value associated with each of the plurality of observation vectors. The target value is an indicator of a characteristic of the associated observation vector. A weight matrix used to predict the characteristic for each of the plurality of variables and each of the plurality of related tasks is computed. (a) and (b) below are repeated with the computed updated weight matrix as the computed weight matrix until a convergence criterion is satisfied:

(a) a gradient descent matrix is computed using the computed plug-in autocovariance matrix, the computed plug-in covariance vector, the computed weight matrix, and a predefined relationship matrix, wherein the predefined relationship matrix defines a relationship between the plurality of related tasks; and (b) an updated weight matrix is computed using the computed gradient descent matrix.

When the convergence criterion is satisfied, the computed updated weight matrix output to predict a value for the characteristic in a scoring dataset.

In another example embodiment, a computing device is provided. The computing device includes, but is not limited to, a processor and a non-transitory computer-readable medium operably coupled to the processor. The computer-readable medium has instructions stored thereon that, when executed by the computing device, cause the computing device to compute the updated weight matrix used to predict the value for the characteristic in the scoring dataset.

In yet another example embodiment, a method of computing the updated weight matrix used to predict the value for the characteristic in the scoring dataset is provided.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described referring to the accompanying drawings, wherein like numerals denote like elements.

DETAILED DESCRIPTION

The described inventive system handles missing data in multi-task learning using graph regularization to capture relatedness between connected tasks. To avoid bias and inaccurate inferences, the described inventive system does not handle missing values separately from the modeling as done using existing methods that impute a value and does not simply delete observations with missing data or replace the missing data with some user specified value. Instead, the described inventive system handles the missing features within the learning process to provide improved results over existing systems in application areas such as object location and recognition in image processing, speech classification, data integration from different web directories, identification of handwritten digits, multiple microarray data integration in bioinformatics, prediction of disease progression, machine monitoring, etc. The described inventive system determines a likelihood that data captured electronically from other devices such as sensors is associated with each possible label after training the model with data that may be incomplete.

Missing features (incomplete data) occur for different reasons in a wide variety of applications. For example, in clinical studies, some patients fail to answer some questions, or measurements of some biospecimens are partially lost at various stages. In bioinformatics, experimentation errors, image corruption, and damage to a slide cause missing gene expression samples. In image processing, objects may be partially obstructed from view result in incomplete observations. In machine performance monitoring for failure, malfunctioning or unreliable sensors in sensor networks may result in missing data.

Figure 1:
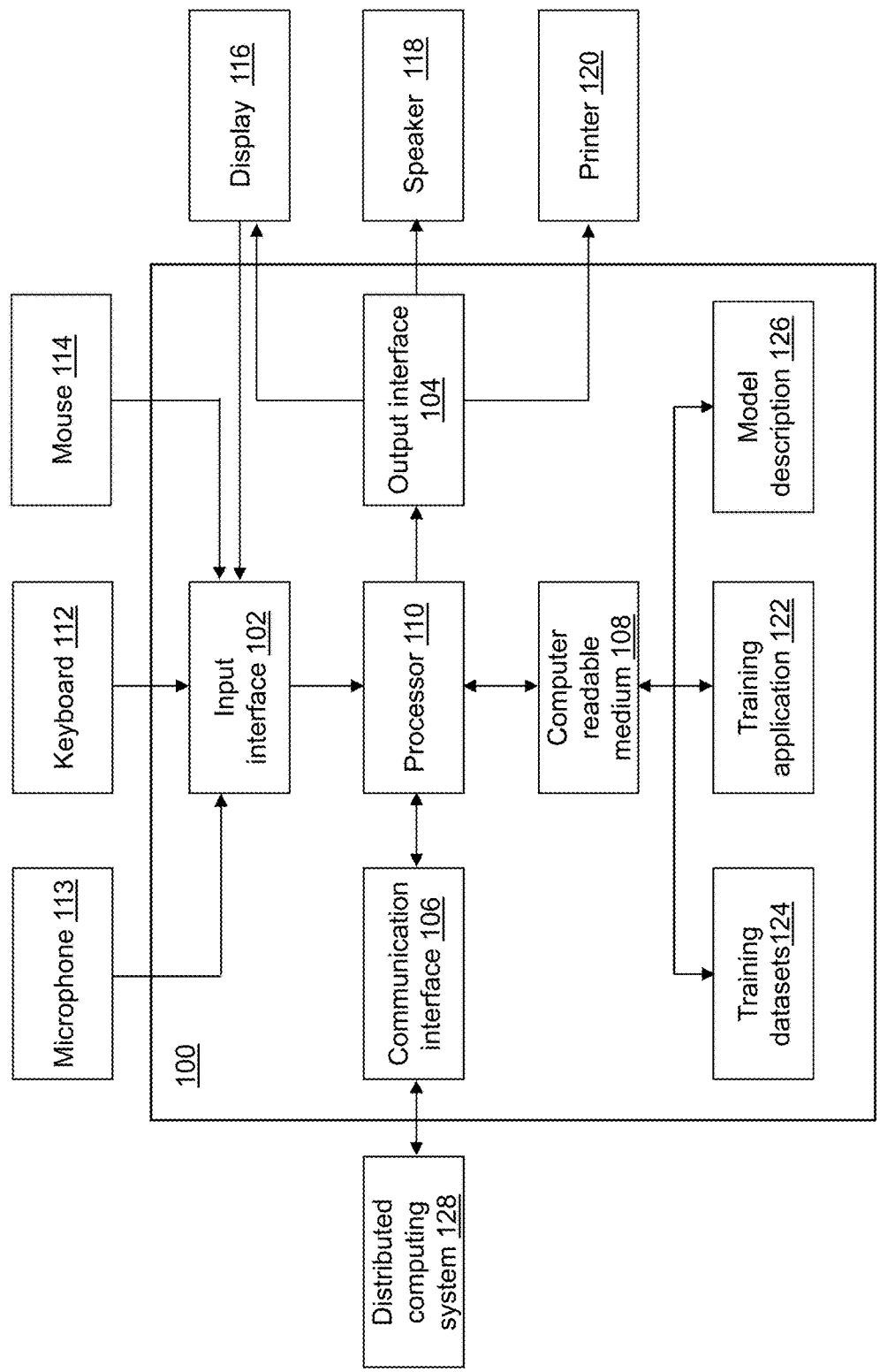
FIG. 1 depicts a block diagram of a model training device in accordance with an illustrative embodiment.

Referring to FIG. 1, a block diagram of a model training device 100 is shown in accordance with an illustrative embodiment. Model training device 100 may include an input interface 102, an output interface 104, a communication interface 106, a non-transitory computer-readable medium 108, a processor 110, a training application 122, a plurality of training datasets 124, and a model description 126. Fewer, different, and/or additional components may be incorporated into model training device 100.

Input interface 102 provides an interface for receiving information from the user or another device for entry into model training device 100 as understood by those skilled in the art. Input interface 102 may interface with various input technologies including, but not limited to, a keyboard 112, a microphone 113, a mouse 114, a display 116, a track ball, a keypad, one or more buttons, etc. to allow the user to enter information into model training device 100 or to make selections presented in a user interface displayed on display 116. The same interface may support both input interface 102 and output interface 104. For example, display 116 comprising a touch screen provides a mechanism for user input and for presentation of output to the user. Model training device 100 may have one or more input interfaces that use the same or a different input interface technology. The input interface technology further may be accessible by model training device 100 through communication interface 106.

Output interface 104 provides an interface for outputting information for review by a user of model training device 100 and/or for use by another application or device. For example, output interface 104 may interface with various output technologies including, but not limited to, display 116, a speaker 118, a printer 120, etc. Model training device 100 may have one or more output interfaces that use the same or a different output interface technology. The output interface technology further may be accessible by model training device 100 through communication interface 106.

Communication interface 106 provides an interface for receiving and transmitting data between devices using various protocols, transmission technologies, and media as understood by those skilled in the art. Communication interface 106 may support communication using various transmission media that may be wired and/or wireless. Model training device 100 may have one or more communication interfaces that use the same or a different communication interface technology. For example, model training device 100 may support communication using an Ethernet port, a Bluetooth antenna, a telephone jack, a USB port, etc. Data and messages may be transferred between model training device 100 and another computing device of a distributed computing system 128 using communication interface 106.

Computer-readable medium 108 is an electronic holding place or storage for information so the information can be accessed by processor 110 as understood by those skilled in the art. Computer-readable medium 108 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disc (CD), digital versatile disc (DVD), . . . ), smart cards, flash memory devices, etc. model training device 100 may have one or more computer-readable media that use the same or a different memory media technology. For example, computer-readable medium 108 may include different types of computer-readable media that may be organized hierarchically to provide efficient access to the data stored therein as understood by a person of skill in the art. As an example, a cache may be implemented in a smaller, faster memory that stores copies of data from the most frequently/recently accessed main memory locations to reduce an access latency. Model training device 100 also may have one or more drives that support the loading of a memory media such as a CD, DVD, an external hard drive, etc. One or more external hard drives further may be connected to model training device 100 using communication interface 106.

Processor 110 executes instructions as understood by those skilled in the art. The instructions may be carried out by a special purpose computer, logic circuits, or hardware circuits. Processor 110 may be implemented in hardware and/or firmware. Processor 110 executes an instruction, meaning it performs/controls the operations called for by that instruction. The term "execution" is the process of running an application or the carrying out of the operation called for by an instruction. The instructions may be written using one or more programming language, scripting language, assembly language, etc. Processor 110 operably couples with input interface 102, with output interface 104, with communication interface 106, and with computer-readable medium 108 to receive, to send, and to process information. Processor 110 may retrieve a set of instructions from a permanent memory device and copy the instructions in an executable form to a temporary memory device that is generally some form of RAM. Model training device 100 may include a plurality of processors that use the same or a different processing technology.

Training application 122 performs operations associated with defining model description 126 from data stored in the plurality of training datasets 124. Model description 126 may be used to classify, to predict and/or to monitor data from data stored in a second dataset 424 (shown referring to FIG. 4). The predicted or classification date may be stored in a predicted dataset 426 (shown referring to FIG. 4) to support various data analysis functions as well as provide alert/messaging related to the monitored data. Some or all of the operations described herein may be embodied in training application 122. The operations may be implemented using hardware, firmware, software, or any combination of these methods.

Referring to the example embodiment of FIG. 1, training application 122 is implemented in software (comprised of computer-readable and/or computer-executable instructions) stored in computer-readable medium 108 and accessible by processor 110 for execution of the instructions that embody the operations of training application 122. Training application 122 may be written using one or more programming languages, assembly languages, scripting languages, etc. Training application 122 may be integrated with other analytic tools. As an example, training application 122 may be part of an integrated data analytics software application and/or software architecture such as that offered by SAS Institute Inc. of Cary, N.C., USA. For example, training application 122 may be may be implemented using or integrated with one or more SAS software tools such as SAS® Enterprise Miner™, SAS® Factory Miner, Base SAS, SAS/STAT®, SAS® High Performance Analytics Server, SAS® LASR™, SAS® In-Database Products, SAS® Scalable Performance Data Engine, SAS/OR®, SAS/ETS®, SAS® Inventory Optimization, SAS® Inventory Optimization Workbench, SAS® Visual Analytics, SAS® Viya™, SAS In-Memory Statistics for Hadoop®, SAS® Forecast Server, SAS® Event Stream Processing (ESP) all of which are developed and provided by SAS Institute Inc. of Cary, N.C., USA. Data mining and data analytics is applicable in a wide variety of industries.

Training application 122 may be integrated with other system processing tools to automatically process data generated as part of operation of an enterprise, device, system, facility, etc., to identify any outliers in the processed data, to monitor changes in the data, and to provide a warning or alert associated with the monitored data using input interface 102, output interface 104, and/or communication interface 106 so that appropriate action can be initiated in response to changes in the monitored data.

Training application 122 may be implemented as a Web application. For example, training application 122 may be configured to receive hypertext transport protocol (HTTP) responses and to send HTTP requests. The HTTP responses may include web pages such as hypertext markup language (HTML) documents and linked objects generated in response to the HTTP requests. Each web page may be identified by a uniform resource locator (URL) that includes the location or address of the computing device that contains the resource to be accessed in addition to the location of the resource on that computing device. The type of file or resource depends on the Internet application protocol such as the file transfer protocol, HTTP, H.323, etc. The file accessed may be a simple text file, an image file, an audio file, a video file, an executable, a common gateway interface application, a Java applet, an extensible markup language (XML) file, or any other type of file supported by HTTP.

The plurality of training datasets 124 includes a training dataset 124*i* for i=1, . . . , K, where K is a number of learning tasks. Each training dataset 124*i* may include, for example, a plurality of rows and a plurality of columns. The plurality of rows may be referred to as observation vectors or records (observations), and the columns may be referred to as variables. Each training dataset 124*i* may be transposed. The plurality of variables may define multiple dimensions for each observation vector. An observation vector $x_{i,j}$ may include a value for each of the plurality of variables associated with the observation j, where j=1, . . . , $N_i$ and i=1, . . . , K, where $N_i$ is a number of observations in training dataset 124*i*. The plurality of training datasets 124 may have different numbers of observations.

Each variable of the plurality of variables $v_i$ describes a characteristic of a physical object. For example, if each training dataset 124*i* includes data related to operation of a vehicle, the variables may include an oil pressure, a speed, a gear indicator, a gas tank level, a tire pressure for each tire, an engine temperature, a radiator level, etc. Each training dataset 124*i* may include data captured as a function of time for one or more physical objects. The plurality of training datasets 124 may have different sets of variables that define each observation vector. Each observation vector $x_{i,j}$ includes observation vector values $o_{i,j,l}$, where l=1, . . . , $v_i$, j=1, . . . , $N_i$, and i=1, . . . , K, where $v_i$ is a number of the plurality of variables that make up each observation vector in training dataset 124*i*. Some observation vector values $o_{i,j,l}$ may be missing. Associated with each observation vector $x_{i,j}$ is a target variable value $y_{i,j}$, where j=1, . . . , $N_i$, and i=1, . . . , K. Less than all of the columns of each training dataset 124*i* may be used as variables that define each observation vector $x_{i,j}$ or target variable value $y_{i,j}$ used to define model description 126. Thus, each training dataset 124*i* may include greater than $v_i$+1 columns. $X_i(j,l)$, i=1, . . . , K, j=1, . . . , $N_i$, and l=1, . . . , $v_i$, where $X_i$ is a matrix of the observation vectors for each of the learning tasks. $y_i(j)$, i=1, . . . , K, and j=1, . . . , $N_i$, where $y_i$ is a target variable vector for each of the learning tasks. $X_i$ and $y_i$ are the portion of training dataset 124*i* used to define model description 126.

The data stored in each training dataset 124*i* may be generated by and/or captured from a variety of sources including one or more sensors of the same or different type, one or more computing devices, etc. The data stored in each training dataset 124*i* may be received directly or indirectly from the source and may or may not be pre-processed in some manner. For example, the data may be pre-processed using an event stream processor such as the SAS® Event Stream Processing Engine (ESPE), developed and provided by SAS Institute Inc. of Cary, N.C., USA. As used herein, the data may include any type of content represented in any computer-readable format such as binary, alphanumeric, numeric, string, markup language, etc. The data may be organized using delimited fields, such as comma or space separated fields, fixed width fields, using a SAS® dataset, etc. The SAS dataset may be a SAS® file stored in a SAS® library that a SAS® software tool creates and processes. The SAS dataset contains data values that are organized as a table of observations (rows) and variables (columns) that can be processed by one or more SAS software tools.

The plurality of training datasets 124 may be stored on computer-readable medium 108 and/or on one or more computer-readable media of distributed computing system 128 and accessed by model training device 100 using communication interface 106, input interface 102, and/or output interface 104. Data stored in the plurality of training datasets 124 may be sensor measurements or signal values captured by a sensor, may be generated or captured in response to occurrence of an event or a transaction, generated by a device such as in response to an interaction by a user with the device, etc. The data stored in the plurality of training datasets 124 may include any type of content represented in any computer-readable format such as binary, alphanumeric, numeric, string, markup language, etc. The content may include textual information, graphical information, image information, audio information, numeric information, etc. that further may be encoded using various encoding techniques as understood by a person of skill in the art. The data stored in the plurality of training datasets 124 may be captured at different time points periodically, intermittently, when an event occurs, etc. One or more columns of the plurality of training datasets 124 may include a time and/or date value.

The plurality of training datasets 124 may include data captured under normal operating conditions of the physical object. The plurality of training datasets 124 may include data captured at a high data rate such as 200 or more observations per second for one or more physical objects. For example, data stored in the plurality of training datasets 124 may be generated as part of the Internet of Things (IoT), where things (e.g., machines, devices, phones, sensors, smart meters for energy, personal wearable devices, health monitoring devices, autonomous vehicle devices, robotic components, identification devices, etc.) can be connected to networks and the data from these things collected and processed within the things and/or external to the things before being stored in one or more of the plurality of training datasets 124. For example, the IoT can include sensors in many different devices and types of devices, and high value analytics can be applied to identify hidden relationships and drive increased efficiencies. This can apply to both big data analytics and real-time analytics. Some of these devices may be referred to as edge devices, and may involve edge computing circuitry. These devices may provide a variety of stored or generated data, such as network data or data specific to the network devices themselves. Again, some data may be processed with an ESPE, which may reside in the cloud or in an edge device before being stored in one or more of the plurality of training datasets 124.

The plurality of training datasets 124 may be stored using various data structures as known to those skilled in the art including one or more files of a file system, a relational database, one or more tables of a system of tables, a structured query language database, etc. on model training device 100 or on distributed computing system 128 that may be the same or different. Model training device 100 may coordinate access to the plurality of training datasets 124 that is distributed across distributed computing system 128 that may include one or more computing devices. For example, the plurality of training datasets 124 may be stored in a cube distributed across a grid of computers as understood by a person of skill in the art. As another example, the plurality of training datasets 124 may be stored in a multi-node Hadoop® cluster. For instance, Apache™ Hadoop® is an open-source software framework for distributed computing supported by the Apache Software Foundation. As another example, the plurality of training datasets 124 may be stored in a cloud of computers and accessed using cloud computing technologies, as understood by a person of skill in the art. The SAS® LASR™ Analytic Server may be used as an analytic platform to enable multiple users to concurrently access data stored in the plurality of training datasets 124. The SAS® Viya™ open, cloud-ready, in-memory architecture also may be used as an analytic platform to enable multiple users to concurrently access data stored in the plurality of training datasets 124. Some systems may use SAS In-Memory Statistics for Hadoop® to read big data once and analyze it several times by persisting it in-memory for the entire session. Some systems may be of other types and configurations.

Figure 2A:
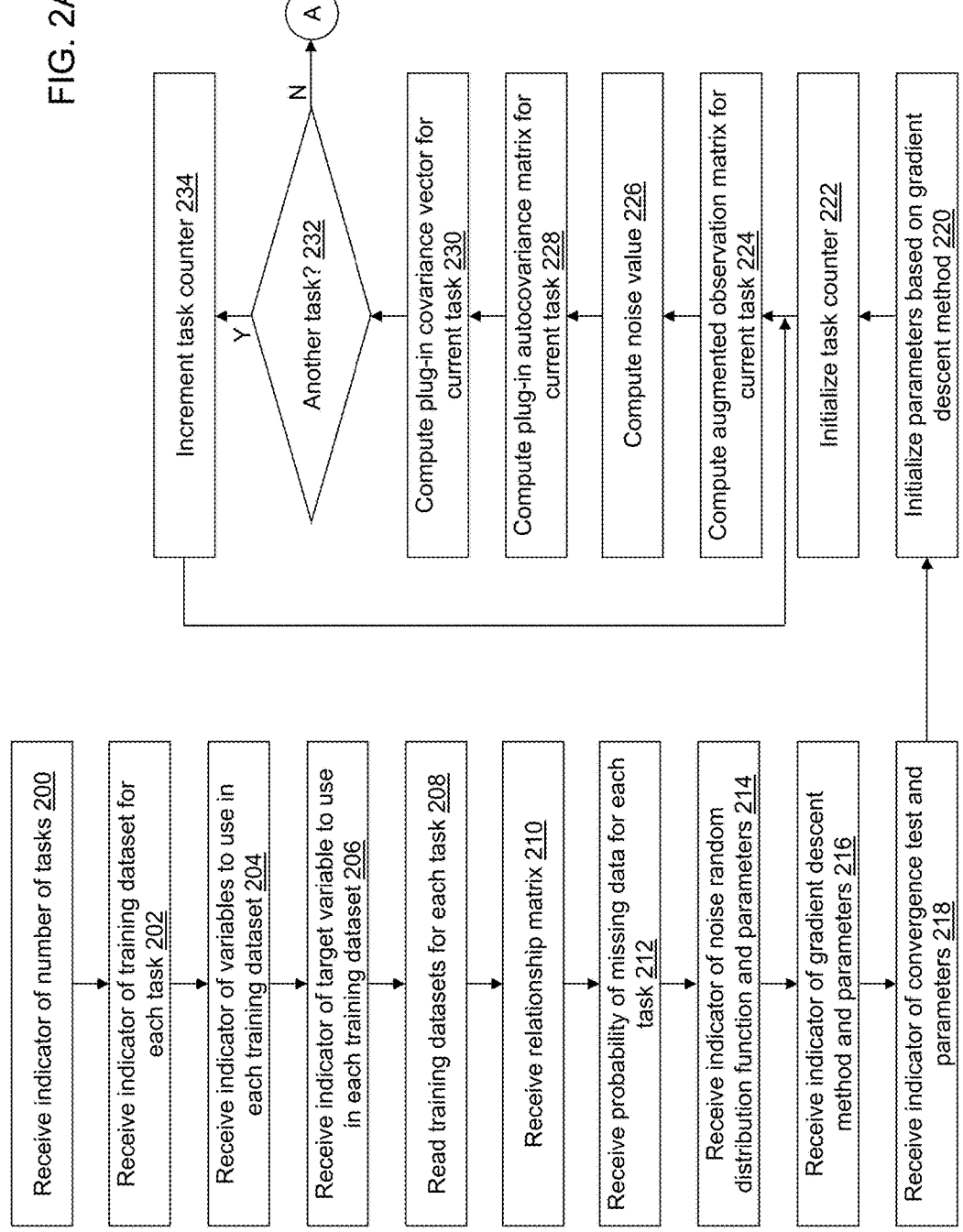
FIGS. 2A, 2B, and 2C depict a flow diagram illustrating examples of operations performed by the model training device of FIG. 1 in accordance with an illustrative embodiment.
Figure 2B:
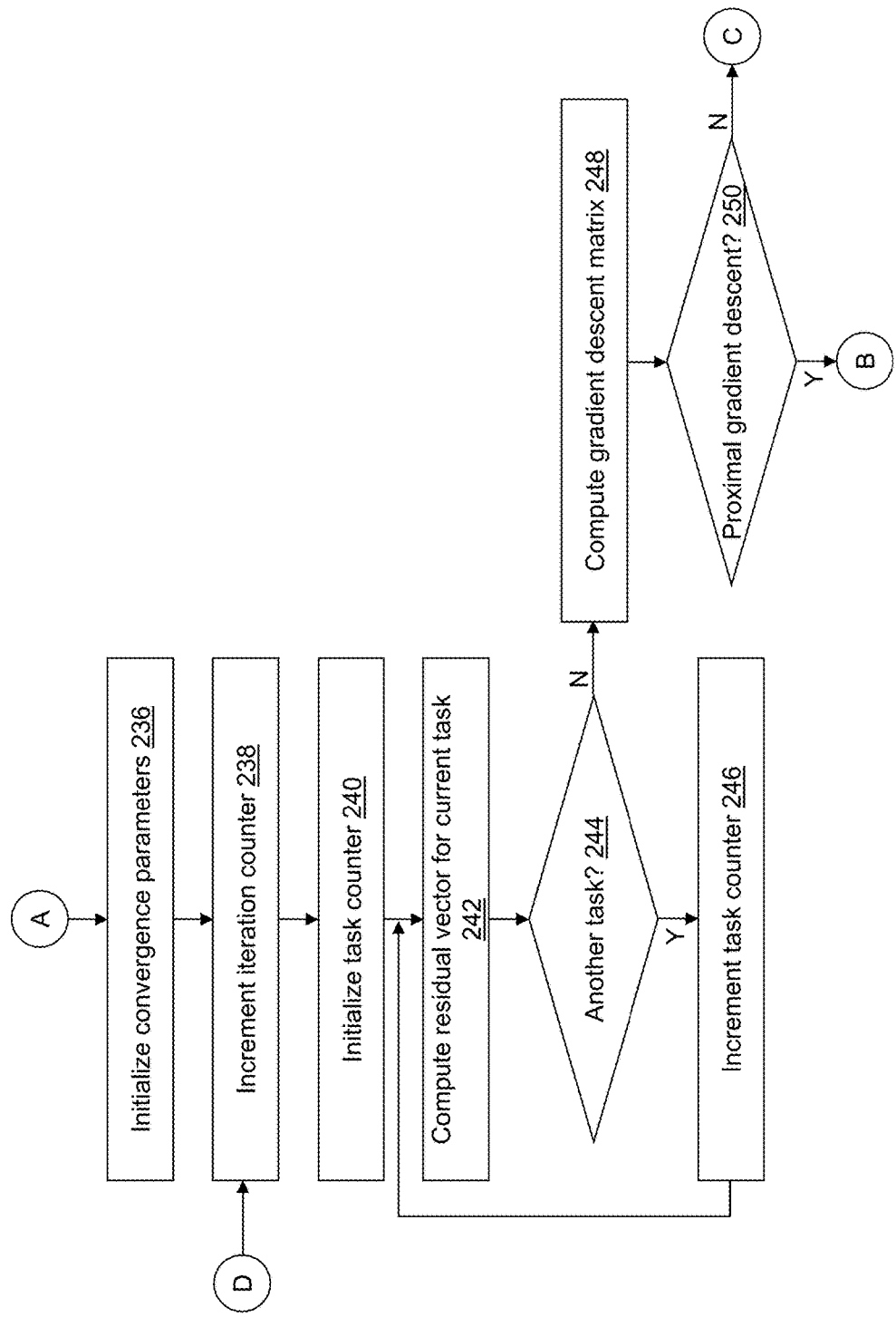
Figure 2C:
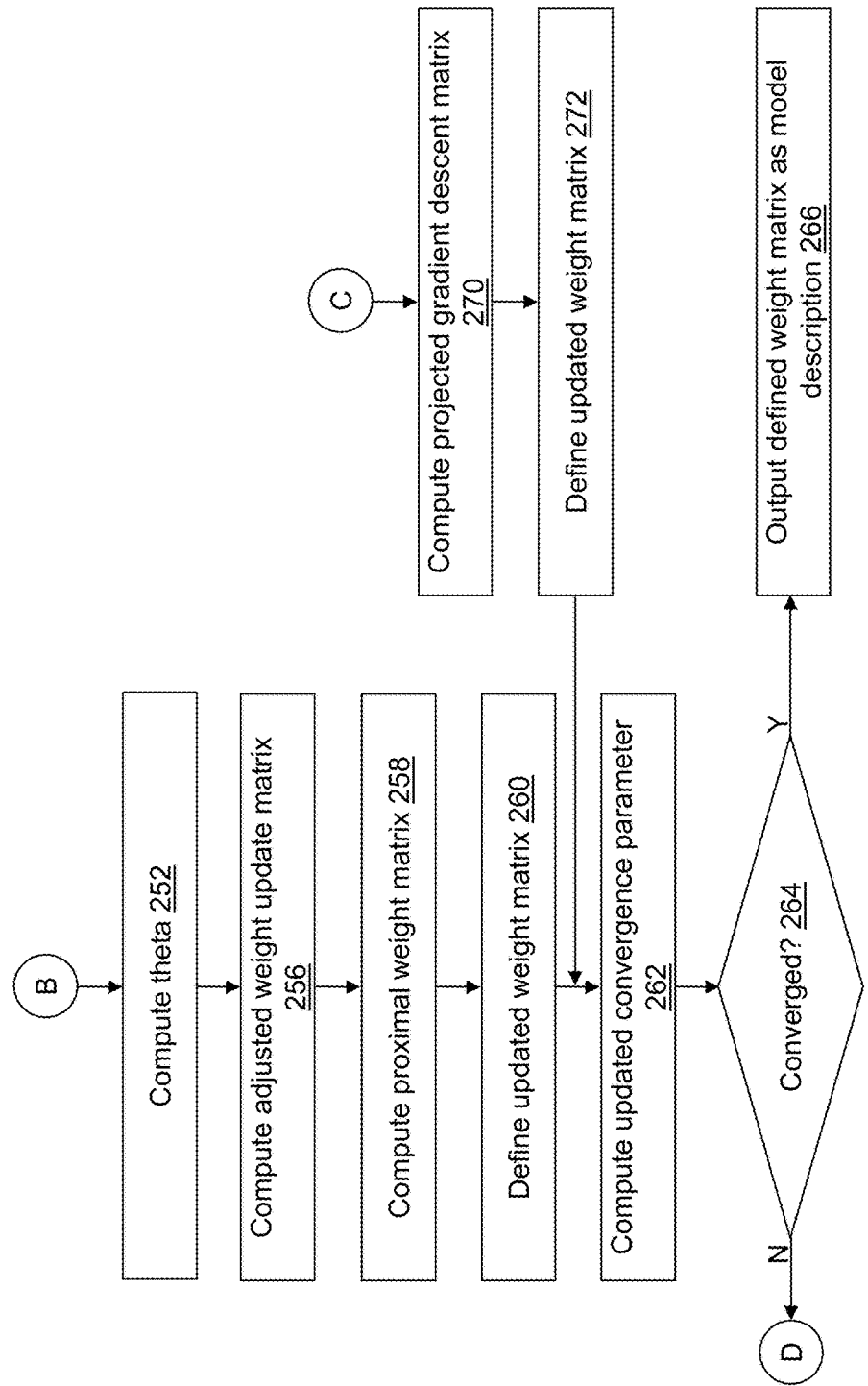

Referring to FIGS. 2A, 2B, and 2C, example operations associated with training application 122 are described. For example, training application 122 may be used to create model description 126 from the plurality of training datasets 124. Additional, fewer, or different operations may be performed depending on the embodiment of training application 122. The order of presentation of the operations of FIGS. 2A, 2B, and 2C is not intended to be limiting. Although some of the operational flows are presented in sequence, the various operations may be performed in various repetitions, concurrently (in parallel, for example, using threads and/or distributed computing system 128), and/or in other orders than those that are illustrated. For example, a user may execute training application 122, which causes presentation of a first user interface window, which may include a plurality of menus and selectors such as drop down menus, buttons, text boxes, hyperlinks, etc. associated with training application 122 as understood by a person of skill in the art. The plurality of menus and selectors may be accessed in various orders. An indicator may indicate one or more user selections from a user interface, one or more data entries into a data field of the user interface, one or more data items read from computer-readable medium 108 or otherwise defined with one or more default values, etc. that are received as an input by training application 122.

Referring to FIG. 2A, in an operation 200, a first indicator may be received that indicates the number of learning tasks K. The first indicator indicates a number of the plurality of training datasets 124. In an alternative embodiment, the first indicator may not be received. For example, a default value may be stored, for example, in computer-readable medium 108 and used automatically. In another alternative embodiment, the value of the number of learning tasks K may not be selectable or received. Instead, the value may be determined automatically based on a number of the plurality of training datasets 124 indicated by the user in an operation 202.

In operation 202, a second indicator may be received that indicates the plurality of training datasets 124. For example, the second indicator indicates a location and a name of the plurality of training datasets 124. As an example, the second indicator may be received by training application 122 after selection from a user interface window or after entry by a user into a user interface window. In an alternative embodiment, the plurality of training datasets 124 may not be selectable. For example, a most recently created dataset may be used automatically. For example, a grid, a cube, a cloud, a Hadoop® cluster, a relational database, a file system, etc. location may be used automatically as a location/name of the plurality of training datasets 124. As mentioned previously, the number of learning tasks K may be determined automatically based on the number of unique datasets included in the grid, cube, cloud, Hadoop® cluster, relational database, file system, etc.

In an operation 204, a third indicator may be received that indicates a plurality of variables $v_i$ associated with each of the plurality of training datasets 124 to define each observation vector $x_{i,j}$. The third indicator may indicate that all or only a subset of the variables stored in each of the plurality of training datasets 124 be used to define model description 126. For example, the third indicator indicates a list of variables to use by name, column number, etc. In an alternative embodiment, the third indicator may not be received. For example, all of the variables except the last variable may be used automatically. The third indicator may define the plurality of variables for each of the plurality of training datasets 124 in the same or a different manner though the set of the plurality of variables $v_i$ is common to each of the plurality of training datasets 124.

In an operation 206, a fourth indicator may be received that indicates a target variable (column) associated with each of the plurality of training datasets 124 to define the target variable vector $y_i$. The target variable may be a label for the associated observation vector. For example, the label may indicate a characteristic determined from the observation vector. For example, the fourth indicator indicates a variable to use by name, column number, etc. In an alternative embodiment, the fourth indicator may not be received. For example, the last variable in training dataset 124$i$ may be used automatically. The fourth indicator may define the target variable for each of the plurality of training datasets 124 in the same or a different manner though the target variable is common to each of the plurality of training datasets 124.

In an operation 208, the plurality of variables $v_i$ and the target variable are read from each of the plurality of training datasets 124 to define the observation matrix $X_i(j,l)$ and the target variable vector $y_i(j)$, i=1, ..., K, j=1, ..., $N_i$, l=1, ..., $v_i$ for each of the K learning tasks. $N_i$ may be the same or different for each of the plurality of training datasets 124. The objective of training application 122 is to learn a model based on $y_i=X_iW_i+\sigma_i$, i=1, ..., K, where $W_i$ is the model made up of weights for each variable and $\sigma_i$ is random noise. Thus, weight matrix W has dimension ($v_i$, K) and defines a covariance matrix that can be used to compute a likelihood that y has a given "label" or possible value based on observed values for the observation vector x. The "label" or possible value is predicted for the observation vector by selecting the label based on a maximum value of the computed likelihood.

In numerous applications, there are multiple tasks labeling the same data instances differently. Multi-task learning uses the relations between multiple tasks by learning all tasks simultaneously to improve the prediction performance and to increases a sample size. For example, in disease progression prediction, a prediction of clinical scores at each visit can be modeled as a regression task with a patient's different visits as separate regression problems that share commonality and are solved simultaneously.

Another example multi-task learning environment includes a forecast demand for electricity for multiple nodes of a distribution network with the goal of identifying the best way to capture the complex seasonal demand patterns. Another example multi-task learning environment includes manufacturing parts in multiple chambers with different conditions with the goal of predicting a quality based on process variables, such as temperature, pressure, etc., diagnosis and prognosis of disease over multiple visits. For example, in semiconductor manufacturing, the wafers have multiple sides that are produced in multiple chambers. Each side can be seen as a single task with a model that predicts the quality of wafers produced therein based on the process variables, and each chamber can be seen as a group of such tasks. Intuitively, the models for different sides of the same chamber are related on the side-level (task-level), whereas the models for different chambers are related on the chamber-level (group-level). Another example multi-task learning environment includes facial landmark detection with different head poses such as front, left, and right. Another example multi-task learning environment includes genetics data from different organism for cell regulations where there is an understanding of how closely related two organisms are that can be used in computational biology. Another example multi-task learning environment includes speech recognition based on gender. Another example multi-task learning environment includes Web search ranking where most major search engines offer specialized rankings for different countries or regions. The different countries as tasks that are not completely independent of each other because they share some commonalities, yet are different enough that their training data sets cannot be naively combined.

Figure 3:
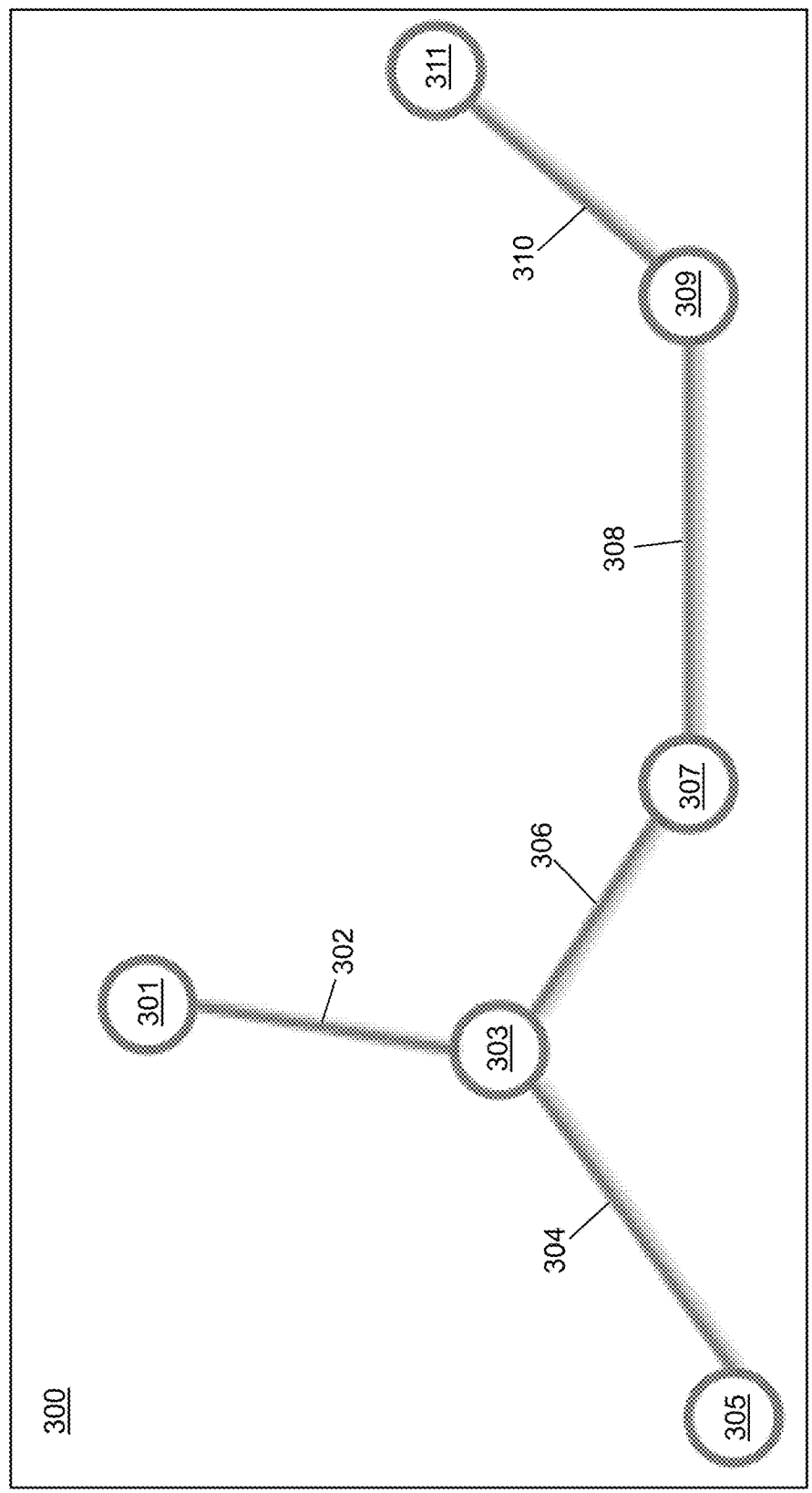
FIG. 3 shows a task relationship graph in accordance with an illustrative embodiment.

In an operation 210, a relationship matrix R is received. For illustration, referring to FIG. 3, a task relationship graph 300 is shown in accordance with an illustrative embodiment. When tasks are "related", the underlying models of the tasks are expected to be similar to each other. Specifically, if task i and task j are related, $W_i$ and $W_j$ are expected to be similar. Task relationship graph 300 may be created by an expert in the field. The relationship between K learning tasks is represented by task relationship graph 300, which is an undirected graph, where each task is a node, and pairs of nodes are connected if the two tasks are related. To encode the connections, let $\varepsilon$ be a set of edges h in the undirected graph. $R \in \mathbb{R}^{K \times |\varepsilon|}$ where $$R_{g,h} = \begin{cases} 1, & \text{if } g < k, \text{ edge } h \text{ connects nodes } g, k, \\ -1, & \text{if } g > k, \text{ edge } h \text{ connects nodes } g, k, \\ 0, & \text{otherwise.} \end{cases}$$

For illustration, the relationship matrix R for task relationship graph 300 is $$R = \begin{bmatrix} 1 & 0 & 0 & 0 & 0 \\ -1 & 1 & 1 & 0 & 0 \\ 0 & -1 & 0 & 0 & 0 \\ 0 & 0 & -1 & 1 & 0 \\ 0 & 0 & 0 & -1 & 1 \\ 0 & 0 & 0 & 0 & -1 \end{bmatrix}$$

where $R_{K,H}$ has dimension K=6 based on the number of tasks, which equals the number of nodes of task relationship graph 300 and H=5 based on the number of edges of task relationship graph 300. For example, task relationship graph 300 includes a first task node 301 connected to a second task node 303 by a first edge 302; a third task node 305 connected to second task node 303 by a second edge 304; a fourth task node 307 connected to second task node 303 by a third edge 306; a fifth task node 309 connected to fourth task node 307 by a fourth edge 308; and a sixth task node 311 connected to fifth task node 309 by a fifth edge 310. Relationship matrix R may be received in various manners such as by reading from a memory location of computer-readable medium 108, from a user defined graph in a user interface presented under control of training application 122, from a user defined matrix in a user interface presented under control of training application 122, etc.

For example, the relationship matrix R for task relationship graph 300 can be defined by estimating a statistical distribution (e.g., Multivariate Gaussian) for each task using the task's data, which can include the target variable, computing a distance, such as a Bhattacharyya distance, between the estimated distributions of the tasks, defining a threshold distance, and, when the distance between two tasks is smaller than the threshold distance, an edge is set between the tasks.

In an operation 212, a fifth indicator may be received that indicates a value of a probability of missing data values of each of the plurality of training datasets 124 to define a probability vector p(i), i=1, . . . , K referred as $p_i$. Each probability value may be received as a percent of missing data such as 10%, 20%, etc. though the percent may be stored in $p_i$ as a decimal value such as 0.1, 0.2, etc. such that $p_i \in (0,1)$ The probability value for each training dataset 124i may be the same or different. For example, a training dataset 124i known to Include data from a faulty sensor may have a higher probability of missing data in comparison to other of the plurality of training datasets 124. In an alternative embodiment, the fifth indicator may not be received. For example, a default value may be stored, for example, in computer-readable medium 108 and used automatically for each training dataset 124i.

In solving the issue of incomplete data, the objective is making accurate and efficient inferences not retrieving missing values. Imputation of missing data points can impair inference. For instance, replacing missing samples with a mean of the observations changes the variance and the correlation. Accordingly, incomplete data cannot be properly addressed separate from model learning. As described further below, training application 122 handles missing data within the learning process using the defined probability vector p(i).

In an operation 214, a sixth indicator of a distribution function with any associated parameters to compute random noise $\sigma_i$ may be received. For example, the sixth indicator indicates a name of a distribution function. The sixth indicator may be received by training application 122 after selection from a user interface window or after entry by a user into a user interface window. A default value for the distribution function may further be stored, for example, in computer-readable medium 108. As an example, a distribution function may be selected from "Gaussian", "Uniform", etc. For example, a default distribution function may be the Uniform distribution function. Of course, the distribution function may be labeled or selected in a variety of different manners by the user as understood by a person of skill in the art. Associated parameters may include a random seed, a maximum value, a minimum value, a mean value, a standard deviation value, etc. based on the type of distribution function used. In an alternative embodiment, the distribution function may not be selectable, and a single distribution function may be implemented in training application 122. For example, the Uniform distribution function may be used by default or without allowing a selection with a minimum value of zero and a maximum value of one.

In an operation 216, a seventh indicator of a gradient descent method with any associated parameters to estimate weight matrix W may be received. For example, the seventh indicator indicates a name of a gradient descent method. The seventh indicator may be received by training application 122 after selection from a user interface window or after entry by a user into a user interface window. A default value for the gradient descent method may further be stored, for example, in computer-readable medium 108. As an example, a gradient descent method may be selected from "Projected", "Accelerated Proximal", etc. For example, a default gradient descent method may be the Accelerated Proximal gradient descent method. Of course, the gradient descent method may be labeled or selected in a variety of different manners by the user as understood by a person of skill in the art. In an alternative embodiment, the gradient descent method may not be selectable, and a single gradient descent method may be implemented in training application 122. For example, the Accelerated Proximal gradient descent method may be used by default or without allowing a selection.

Associated parameters for the Accelerated Proximal gradient descent method may include a step size $\eta$, a graph penalization weight value $\lambda$, and a sparsity penalization weight value $\mu$. For reference, the paper by Amir Beck and Marc Teboulle, *A Fast Iterative Shrinkage-Thresholding Algorithm for Linear Inverse Problems,* 2 SIAM J. IMAGING SCIENCES, 183 (2009) describes the Accelerated Proximal gradient descent method for a single task. For illustration, a range of values for $\eta$ may be $0 \leq \eta \leq 1$ with a default value of $\eta=0.001$. For illustration, a range of values for $\lambda$ may be $0 \leq \lambda \leq 1000$ with a default value of $\lambda=0.1$. For illustration, a range of values for $\mu$ may be $0 \leq \mu \leq 1000$ with a default value of $\mu=0.1$.

Associated parameters for the Projected gradient descent method may include the penalization weight values $\mu$ and $\lambda$. For reference, the paper by Po-Ling Loh and Martin J. Wainwright, *High-Dimensional Regression With Noisy and Missing Data: Provable Guarantees With Non-Convexity,* 40 The Annals of Statistics, 1637 (2012) describes the Projected gradient descent method for a single task. In general, the Accelerated Proximal gradient descent method converges faster than the Projected gradient descent method.

In an operation 218, an eighth indicator of a convergence test with any associated parameters to determine when the estimation of $W_i$ is complete may be received. For example, the eighth indicator indicates a name of a convergence test. The eighth indicator may be received by training application 122 after selection from a user interface window or after entry by a user into a user interface window. A default value for the convergence test may further be stored, for example, in computer-readable medium 108. As an example, a convergence test may be selected from "Max Iterations", "Relative Change", "Both Iterations and Change", etc. For example, a default convergence test may be "Both Iterations and Change". Of course, the convergence test may be labeled or selected in a variety of different manners by the user as understood by a person of skill in the art. In an alternative embodiment, the convergence test may not be selectable, and a single convergence test is implemented by training application 122. For example, the convergence test "Both Iterations and Change" may be used by default or without allowing a selection.

Associated parameters for the convergence may include a value of a maximum number of iterations M and a tolerance value $\epsilon_W$. Default values for either or both may be stored, for example, in computer-readable medium 108 and used automatically. The tolerance value $\epsilon_W$ may be identified as a first stop criterion, and the maximum number of iterations M may be identified as a second stop criterion. For example, the maximum number of iterations M may be selected to stop execution when convergence is not being reached. Merely for illustration, the maximum number of iterations M may be set between 10 and 1000 though the user may determine that other values are more suitable for their application as understood by a person of skill in the art, for example, based on the accuracy desired, computing resources available, etc.

In an operation 220, parameters are initialized based on the gradient descent method selected. For example, for both the Projected gradient descent method and the Accelerated Proximal gradient descent method, an estimated weight matrix $\hat{W}^0$ may be initialized using small random values that may be l1 normalized after making the random draws. The random values may be based on the random noise distribution function of operation 214 or another distinct distribution function selected by a user or implemented by default.

In an operation 222, a task counter i may be initialized as a current task. For example, i may be initialized to one.

In an operation 224, an augmented observation matrix $Z_i$ is computed for the current task i based on the probability vector $p_i$ using $$Z_i = \frac{1}{1-p_i} X_i,$$

where $Z_i$ has dimension $(N_i, v_i)$.

In an operation 226, a random noise value for $\sigma_i$ is computed using the distribution function of operation 214.

In an operation 228, a plug-in autocovariance matrix $\Gamma_i$ is computed for the current task i based on $\sigma_i$ using $$\Gamma_i = \frac{1}{\sigma_i} Z_i^T Z_i - \frac{p_i}{\sigma_i} \text{diag}(Z_i),$$

where $\Gamma_i$ has dimension $(v_i, v_i)$.

In an operation 230, a plug-in covariance vector $\gamma_i$ is computed for the current task i based on $\sigma_i$ using $$\gamma_i - \frac{1}{\sigma_i} Z_i^T y_i),$$

where $\gamma_i$ has dimension $(v_i)$.

In an operation 232, a determination is made concerning whether or not there is another task. When there is another task i≤K, processing continues in an operation 234. When there is not another task i>K, processing continues in an operation 236 to solve the optimization problem $$\hat{W} = \underset{W}{\text{argmin}} \sum_{i=1}^{K} \left( \frac{1}{2\sigma_i} W_i^T \Gamma_i W_i - \frac{1}{\sigma_i} W_i^T \gamma_i \right) + \frac{\mu}{2} \|W\|_1 + \frac{\lambda}{2} \|WR\|_F^2.$$

In operation 234, task counter i is incremented based on i=i+1 and processing continues in operation 224 to repeat the computations for the next task as the current task.

Referring to FIG. 2B, in operation 236, convergence parameters may be initialized depending on the selection in operation 218, For example, an iteration counter t may be initialized to zero and/or a difference value may be initialized to a large number.

In an operation 238, iteration counter t is incremented based on t=t+1.

In an operation 240, the task counter i may be re-initialized as a current task. For example, i may be re-initialized to one.

In an operation 242, a residual vector $\hat{\nabla}_i$ is computed for the current task i using $\hat{\nabla}_i = \Gamma_i \hat{W}_i^{t-1} - \gamma_i$, where $\hat{\nabla}_i$ has dimension $(v_i)$.

In an operation 244, a determination is made concerning whether or not there is another task. When there is another task i≤K, processing continues in an operation 246. When there is not another task i>K, processing continues in an operation 248.

In operation 246, task counter i is incremented based on i=i+1 and processing continues in operation 242 to repeat the computation for the next task as the current task.

In operation 248, a gradient descent matrix W is computed using $W = \hat{W}^{t-1} - \eta(\tilde{\nabla}(l,i) + \lambda \hat{W}^{t-1} (l,i) R(i,h) R^T(h,i))$, where l=1, ..., $v_i$, h=1, ..., H, and i=1, ..., K.

In an operation 250, a determination is made concerning which gradient descent method is used to update the estimate of the weight matrix $\hat{W}$ using $\tilde{W}$. When the Accelerated Proximal gradient descent method is used, processing continues in an operation 252. When the Projected gradient descent method is used, processing continues in an operation 270. Of course, if only one method is implemented by training application 122, there is no determination, and processing continues based on the implemented method. Of course, if more than two methods are selectable, the determination selection is between the implemented methods, and processing continues based on the selected method. The Projected and the Accelerated Proximal gradient descent methods are illustrative methods for computing the updated, estimated weight matrix.

Referring to FIG. 2C, in operation 252, a theta value $\theta_t$ is computed using $$\theta_t = \frac{1}{2t}.$$

In an operation 256, an adjusted weight update matrix V is computed using $$V = \frac{\theta_t(1 - \theta_{t-1})}{\theta_{t-1}} (\hat{W}^{t-1} - \hat{W}^{t-2}),$$

where V has dimension $(v_i, K)$.

In an operation 258, a proximal weight matrix $$\text{prox}\frac{\eta\mu}{2}(U)$$

is computed using $$\left(\text{prox}_{\frac{\eta\mu}{2}}(U)\right)_{l,i} = \begin{cases} U_{l,i} - \frac{\eta\mu}{2}, & \text{when } U_{l,i} \geq \frac{\eta\mu}{2} \\ 0, & \text{when } |U_{l,i}| < \frac{\eta\mu}{2} \\ \frac{\eta\mu}{2} - U_{l,i}, & \text{when } U_{l,i} \leq -\frac{\eta\mu}{2} \end{cases}$$

and $U(l,i) = [\tilde{W}(l,i) + V(l,i)]$, where l=1, ..., v and i=1, ..., K.

In an operation 260, the updated weight matrix is defined using $$\hat{W}^t = \text{prox}_{\frac{\eta\mu}{2}}(U).$$

In an operation 262, an updated convergence value is computed if needed. For example, if the tolerance value $\epsilon_W$ was specified as a convergence parameter in operation 218, a convergence value is computed based on $\hat{W}^t$. For illustration, a convergence value may be $cv = \|\hat{W}^t - \hat{W}^{t-1}\|_F^2$.

In an operation 264, a determination is made concerning whether or not the weight matrix has converged to a solution. When the weight matrix has converged to a solution, processing continues in an operation 266. When the weight matrix has not converged to a solution, processing continues in operation 238 to compute another estimate of $\hat{W}^t$. For example, convergence may be determined when t>M and/or when $cv \le \epsilon_{\hat{W}}$.

In operation 266, the defined weight matrix $\hat{W}=\hat{W}^t$ and $\hat{W}^{t-1}$ are stored in model description 126 as model W. Older estimates of $\hat{W}$ may be discarded unless a history is requested.

In operation 270, the projected gradient descent matrix proj(U) is computed using $proj(U)=\Pi_r W(l,i)$. For example, the columns of W are concatenated into one vector having dimension Kv, and the algorithm for projection onto the simplex described in a paper by Duchi, J., et al., *Efficient Projections onto the l1-Ball for Learning in High Dimensions*, Proceedings of the 25th international conference on Machine learning, 272-279 (Jul. 5-9, 2008) is performed. The results are reshaped back into $\hat{W}(l,i)$.

In an operation 272, the updated weight matrix is defined using $\hat{W}^t=proj(U)$, and processing continues in operation 262 to test for convergence.

Various operations and combinations of operations of training application 122 may be performed in parallel using multiple threads.

Figure 4:
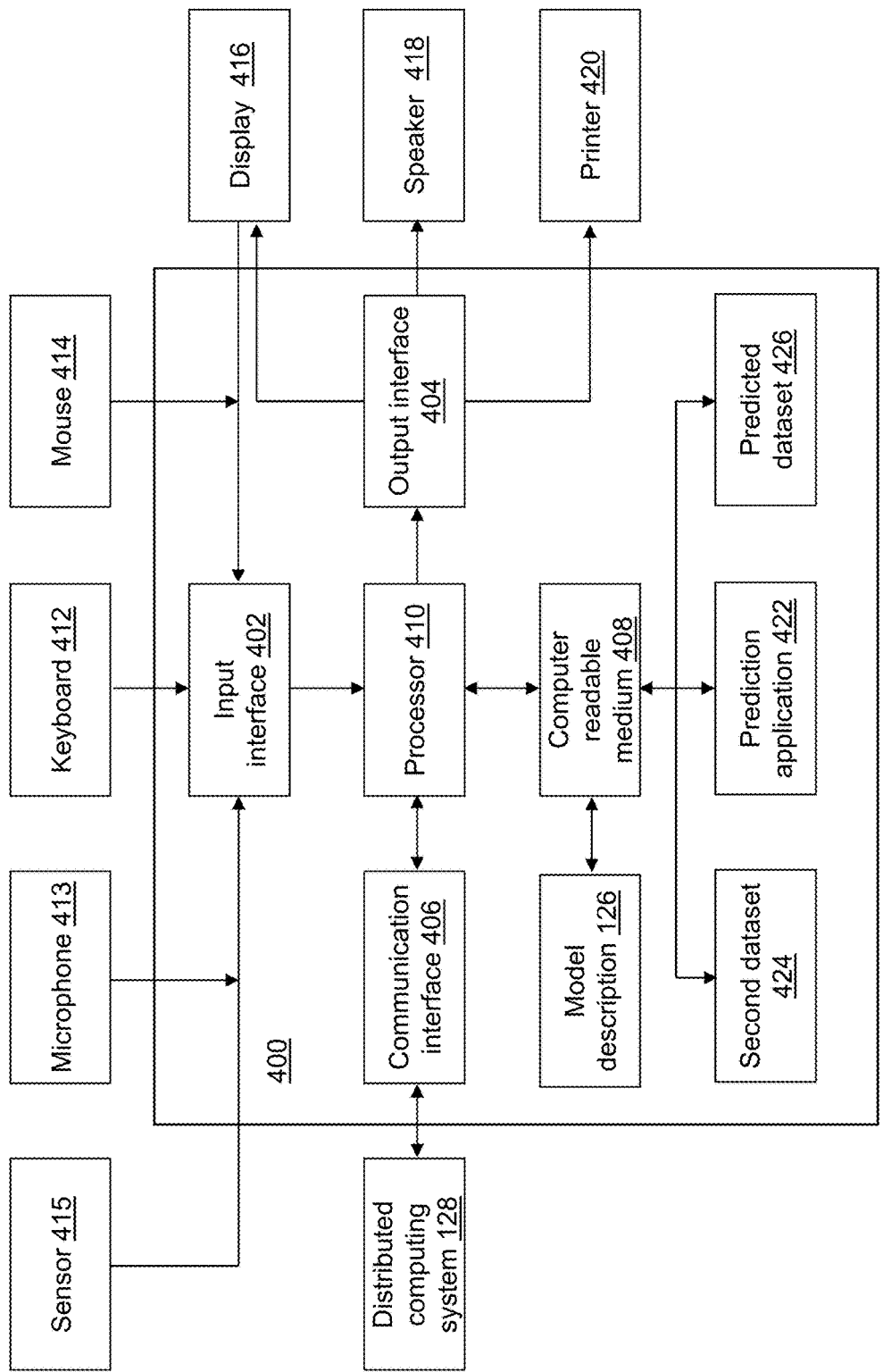
FIG. 4 depicts a block diagram of a prediction device in accordance with an illustrative embodiment.

Referring to FIG. 4, a block diagram of a prediction device 400 is shown in accordance with an illustrative embodiment. Prediction device 400 may include a second input interface 402, a second output interface 404, a second communication interface 406, a second non-transitory computer-readable medium 408, a second processor 410, a prediction application 422, model description 126, a second dataset 424, and a predicted dataset 426. Fewer, different, and/or additional components may be incorporated into prediction device 400. Prediction device 400 and model training device 100 may be the same or different devices.

Second input interface 402 provides the same or similar functionality as that described with reference to input interface 102 of model training device 100 though referring to prediction device 400. Second output interface 404 provides the same or similar functionality as that described with reference to output interface 104 of model training device 100 though referring to prediction device 400. Second communication interface 406 provides the same or similar functionality as that described with reference to communication interface 106 of model training device 100 though referring to prediction device 400. Data and messages may be transferred between prediction device 400 and distributed computing system 128 using second communication interface 406. Second computer-readable medium 408 provides the same or similar functionality as that described with reference to computer-readable medium 108 of model training device 100 though referring to prediction device 400. Second processor 410 provides the same or similar functionality as that described with reference to processor 110 of model training device 100 though referring to prediction device 400.

Prediction application 422 performs operations associated with classifying or predicting a characteristic from data stored in second dataset 424 which may be stored in predicted dataset 426 to support various data analysis functions as well as provide alert/messaging related to the classified/predicted data. Dependent on the type of data stored in the plurality of training datasets 124 and in second dataset 424, prediction application 422 may identify anomalies as part of process control, for example, of a manufacturing process, for machine condition monitoring, for example, an electrocardiogram device, for image classification, for intrusion detection, for fraud detection, etc. Some or all of the operations described herein may be embodied in prediction application 422. The operations may be implemented using hardware, firmware, software, or any combination of these methods.

Referring to the example embodiment of FIG. 4, prediction application 422 is implemented in software (comprised of computer-readable and/or computer-executable instructions) stored in second computer-readable medium 408 and accessible by second processor 410 for execution of the instructions that embody the operations of prediction application 422. Prediction application 422 may be written using one or more programming languages, assembly languages, scripting languages, etc. Prediction application 422 may be integrated with other analytic tools. As an example, prediction application 422 may be part of an integrated data analytics software application and/or software architecture such as that offered by SAS Institute Inc. of Cary, N.C., USA. For example, prediction application 422 may be part of SAS® Enterprise Miner™ developed and provided by SAS Institute Inc. of Cary, N.C., USA that may be used to create highly accurate predictive and descriptive models based on analysis of vast amounts of data from across an enterprise. Merely for further illustration, prediction application 422 may be implemented using or integrated with one or more SAS software tools such as Base SAS, SAS/STAT®, SAS® Enterprise Miner, SAS® Factory Miner, SAS® High Performance Analytics Server, SAS® LASR™, SAS® In-Database Products, SAS® Scalable Performance Data Engine, SAS/OR®, SAS/ETS®, SAS® Inventory Optimization, SAS® Inventory Optimization Workbench, SAS® Visual Analytics, SAS® Viya™, SAS In-Memory Statistics for Hadoop®, SAS® Forecast Server, all of which are developed and provided by SAS Institute Inc. of Cary, N.C., USA. One or more operations of prediction application 422 further may be performed by an ESPE. Prediction application 422 and training application 122 may be the same or different applications that are integrated in various manners.

Prediction application 422 may be implemented as a Web application. Prediction application 422 may be integrated with other system processing tools to automatically process data generated as part of operation of an enterprise, to classify data in the processed data, and/or to provide a warning or alert associated with the data classification using second input interface 402, second output interface 404, and/or second communication interface 406 so that appropriate action can be initiated in response. For example, a warning or an alert may be presented using a second display 416, a second speaker 418, a second printer 420, etc. or sent to one or more computer-readable media, display, speaker, printer, etc. of distributed computing system 128.

The plurality of training datasets 124 and second dataset 424 may be generated, stored, and accessed using the same or different mechanisms. Similar to the plurality of training datasets 124, second dataset 424 may include a plurality of rows and a plurality of columns with the plurality of rows referred to as observations or records, and the columns referred to as variables that are associated with an observation. Second dataset 424 may be transposed.

Similar to the plurality of training datasets 124, second dataset 424 may be stored on second computer-readable medium 408 or on one or more computer-readable media of distributed computing system 128 and accessed by prediction device 400 using second communication interface 406. Data stored in second dataset 424 may be a sensor measurement or a data communication value, for example, from a sensor 415, may be generated or captured in response to occurrence of an event or a transaction, generated by a device such as in response to an interaction by a user with the device, for example, from a second keyboard 412, a second microphone 413, or a second mouse 414, etc.

The data stored in second dataset 424 may include any type of content represented in any computer-readable format such as binary, alphanumeric, numeric, string, markup language, etc. The content may include textual information, graphical information, image information, audio information, numeric information, etc. that further may be encoded using various encoding techniques as understood by a person of skill in the art. The data stored in second dataset 424 may be captured at different time points periodically, intermittently, when an event occurs, etc. One or more columns may include a time value. Similar to the plurality of training datasets 124, data stored in second dataset 424 may be generated as part of the IoT, and some or all data may be pre- or post-processed by an ESPE.

Similar to the plurality of training datasets 124, second dataset 424 may be stored in various compressed formats such as a coordinate format, a compressed sparse column format, a compressed sparse row format, etc. Second dataset 424 further may be stored using various structures as known to those skilled in the art including a file system, a relational database, a system of tables, a structured query language database, etc. on prediction device 400 and/or on distributed computing system 128. Prediction device 400 and/or distributed computing system 128 may coordinate access to second dataset 424 that is distributed across a plurality of computing devices that make up distributed computing system 128. For example, second dataset 424 may be stored in a cube distributed across a grid of computers as understood by a person of skill in the art. As another example, second dataset 424 may be stored in a multi-node Hadoop® cluster. As another example, second dataset 424 may be stored in a cloud of computers and accessed using cloud computing technologies, as understood by a person of skill in the art. The SAS® LASR™ Analytic Server and/or SAS® Viya™ may be used as an analytic platform to enable multiple users to concurrently access data stored in second dataset 424.

Figure 5:
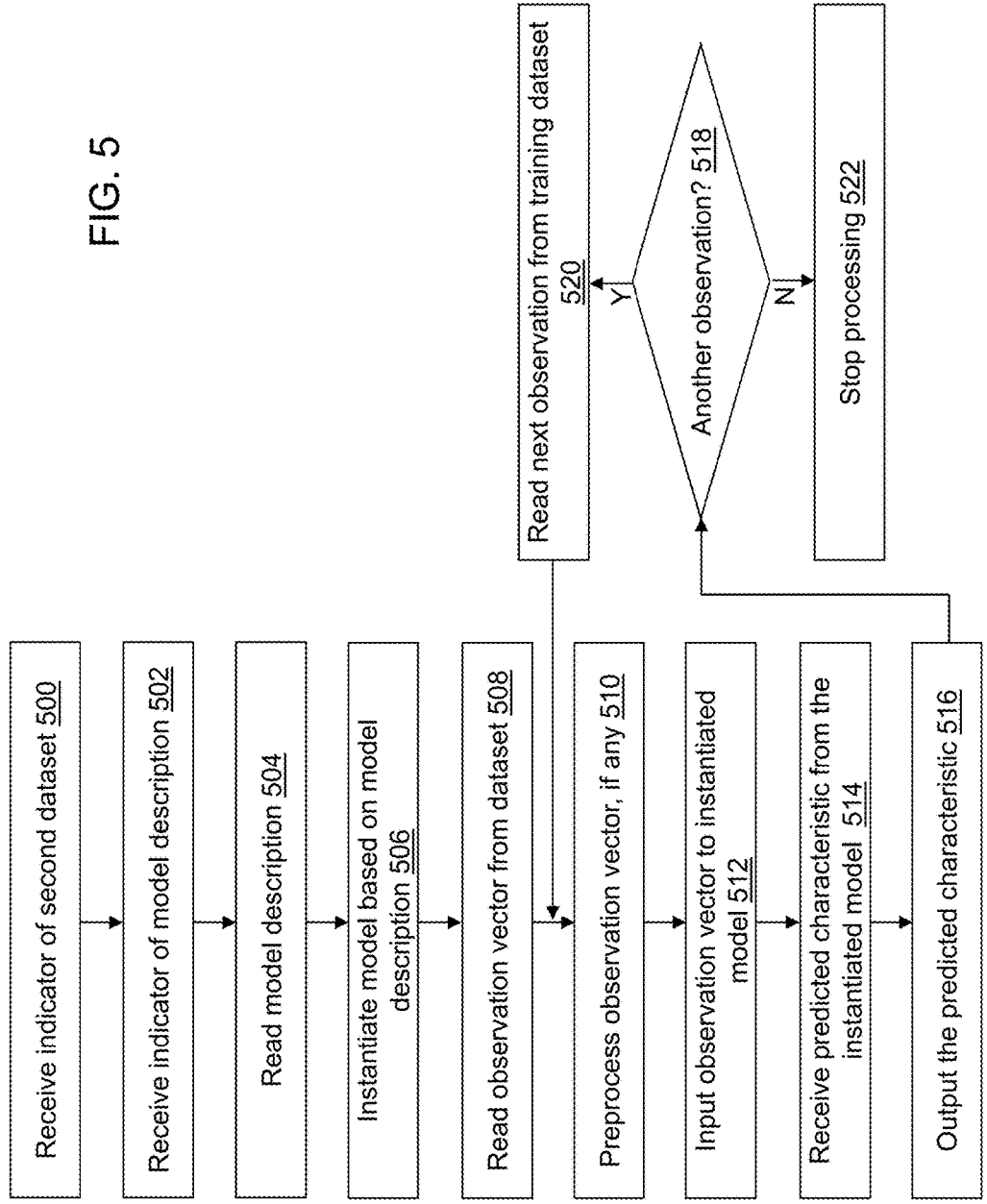
FIG. 5 depicts a flow diagram illustrating examples of operations performed by the prediction device of FIG. 4 in accordance with an illustrative embodiment.

Referring to FIG. 5, example operations of prediction application 422 are described. Additional, fewer, or different operations may be performed depending on the embodiment of prediction application 422. The order of presentation of the operations of FIG. 5 is not intended to be limiting. Although some of the operational flows are presented in sequence, the various operations may be performed in various repetitions, concurrently (in parallel, for example, using threads and/or a distributed computing system), and/or in other orders than those that are illustrated.

In an operation 500, a ninth indicator may be received that indicates second dataset 424. For example, the ninth indicator indicates a location and a name of second dataset 424. As an example, the ninth indicator may be received by prediction application 422 after selection from a user interface window or after entry by a user into a user interface window. In an alternative embodiment, second dataset 424 may not be selectable. For example, a most recently created dataset may be used automatically.

In an operation 502, a tenth indicator may be received that indicates model description 126. For example, the tenth indicator indicates a location and a name of model description 126. As an example, the tenth indicator may be received by prediction application 422 after selection from a user interface window or after entry by a user into a user interface window. In an alternative embodiment, model description 126 may not be selectable. For example, a most recently created model description may be used automatically. As another example, model description 126 may be provided automatically as part of integration with training application 122.

In an operation 504, a regression model description is read from model description 126.

In an operation 506, a regression model is instantiated with the regression model description. For example, the weights are read and used to instantiate the regression model.

In an operation 508, an observation vector is read from second dataset 424.

In an operation 510, the observation vector is pre-processed, if any pre-processing is performed.

In an operation 512, the optionally pre-processed observation vector is input to the instantiated model.

In an operation 514, an output of the instantiated model is received. The output may indicate a predicted characteristic computed from the observation vector using the instantiated model.

In an operation 516, the predicted characteristic may be output, for example, by storing the predicted characteristic with the observation vector to predicted dataset 426. In addition, or in the alternative, the predicted characteristic may be presented on second display 416, printed on second printer 420, sent to another computing device using second communication interface 406, an alarm or other alert signal may be sounded through second speaker 418, etc.

In an operation 518, a determination is made concerning whether or not second dataset 424 includes another observation vector. When second dataset 424 includes another observation vector, processing continues in an operation 520. When second dataset 424 does not include another observation vector, processing continues in an operation 522.

In operation 520, a next observation vector is read from second dataset 424, and processing continues in operation 510.

In operation 522, processing stops and cleanup is performed as needed.

Training application 122 was executed with both synthetic and real datasets as the plurality of training datasets 124. The results computed using training application 122 with projected gradient descent as the gradient descent method are referred to herein as a first method R-LGR. The results were compared with two benchmark methods. A second method referred to herein as LGR filled in missing values of the plurality of training datasets 124 with a zero value and estimated the weight matrix using a standard least absolute shrinkage and selection operator (LASSO) with graph penalization. For reference, the paper by Zhou, J., et al., MALSAR: Multi-tAsk Learning via StructurAl Regularization, Arizona State University, Apr. 23, 2012, describes estimating the weight matrix using standard LASSO with graph penalization. The second method can also be implemented by setting $p_i=0$ for all i regardless of the actual missing percentage. A third method referred to herein as MF-LGR filled in missing values of the plurality of training datasets 124 using a matrix factorization algorithm and estimated the weight matrix using standard LASSO with graph penalization. For reference, the paper by Raghunandan H. Keshavan, et al., *Matrix Completion From a Few Entries*, 56 IEEE Transactions on Information Theory, 2980 (2009) describes the matrix factorization algorithm.

In a first experiment, five tasks were generated with a graph structure with each task feeding into the next. For each of the five training datasets 124, 500 observation vectors were randomly generated for 128 variables. For each task, the weight matrix i=1, . . . , 5 is 11-sparse. Each point value was averaged over 100 random realizations. FM-LGR was not executed because the five training datasets 124 were full rank, and matrix factorization would not have been able to accurately recover the missing values. Using LGR and R-LGR, r is a tuning parameter. In real life, the value of $\|W\|_1$ is often unknown. To illustrate the effect of different choices of r, results were computed with three different levels of r ($0.9\|W\|_1$, $\|W\|_1$, and $1.1\|W\|_1$).

Figure 6:
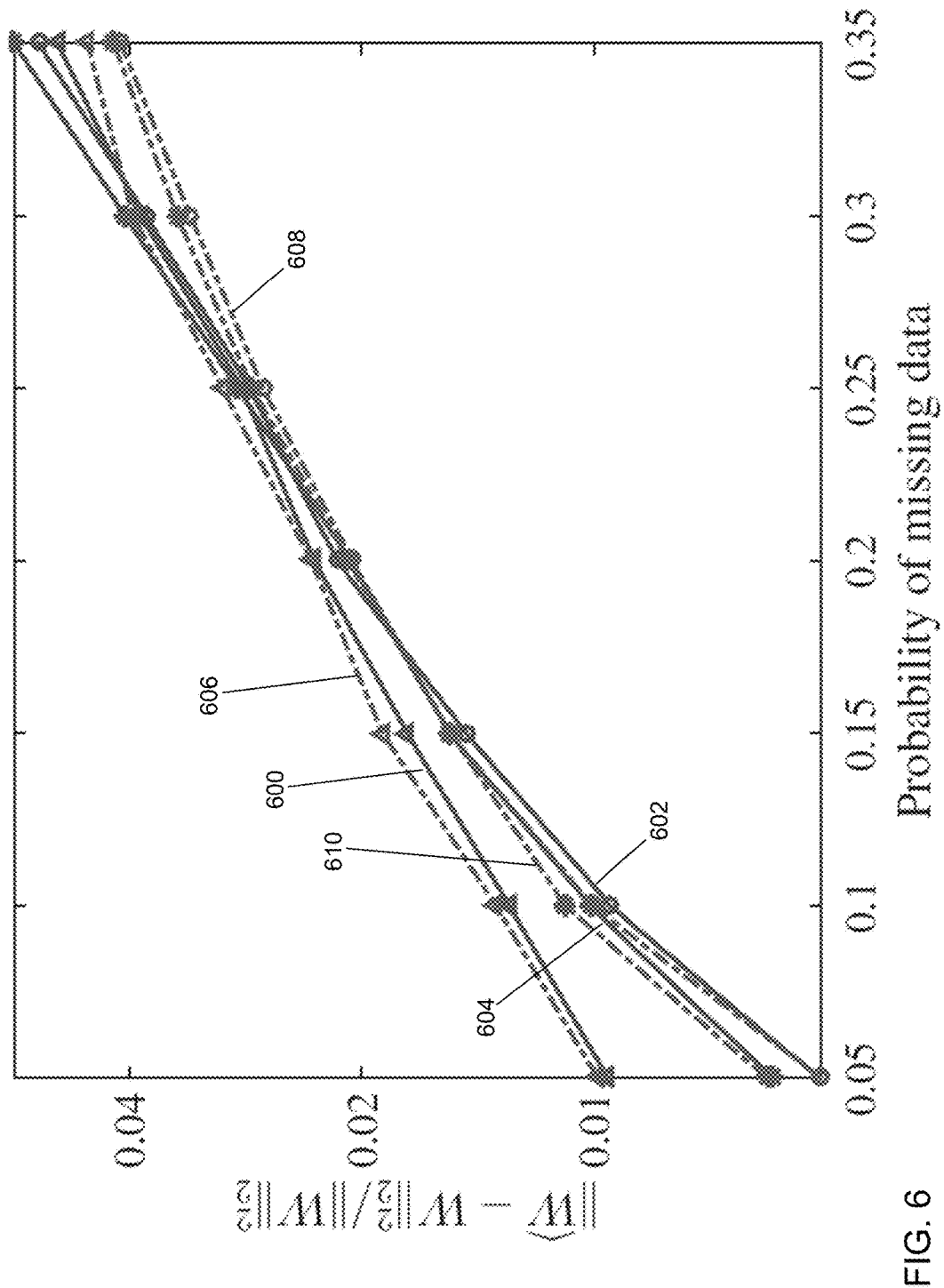
FIG. 6 shows a normalized mean square error of the model weights as a function of a percentage of missing data in accordance with an illustrative embodiment.

Referring to FIG. 6, a normalized mean square error (NMSE) computed for $\hat{W}$ as $\|\hat{W}-W\|_2^2/\|W\|_2^2$ is shown as a function of the probability of missing data $p_i$. A first NMSE curve 600 (solid line with triangles) shows the NMSE of $\hat{W}$ computed using R-LGR with $r=0.9\|W\|_1$. A second NMSE curve 602 (solid line with circles) shows the NMSE of $\hat{W}$ computed using R-LGR with $r=\|W\|_1$. A third NMSE curve 604 (solid line with asterisks) shows the NMSE of $\hat{W}$ computed using R-LGR with $r=1.1\|W\|$. A fourth NMSE curve 606 (dashed line with triangles) shows the NMSE of $\hat{W}$ computed using LGR with $r=0.9\|W\|_1$. A fifth NMSE curve 608 (dashed line with circles) shows the NMSE of $\hat{W}$ computed using LGR with $r=\|W\|_1$. A sixth NMSE curve 610 (dashed line with asterisks) shows the NMSE of W computed using LGR with $r=1.1\|W\|_1$. R-LGR and LGR perform comparably in terms of NMSE, where R-LGR tends to have a smaller NMSE when the probability of missing data $p_i$ is less than 20%, while LGR tends to perform better when the probability of missing data $p_i$ is greater than 20%.

Figure 7:
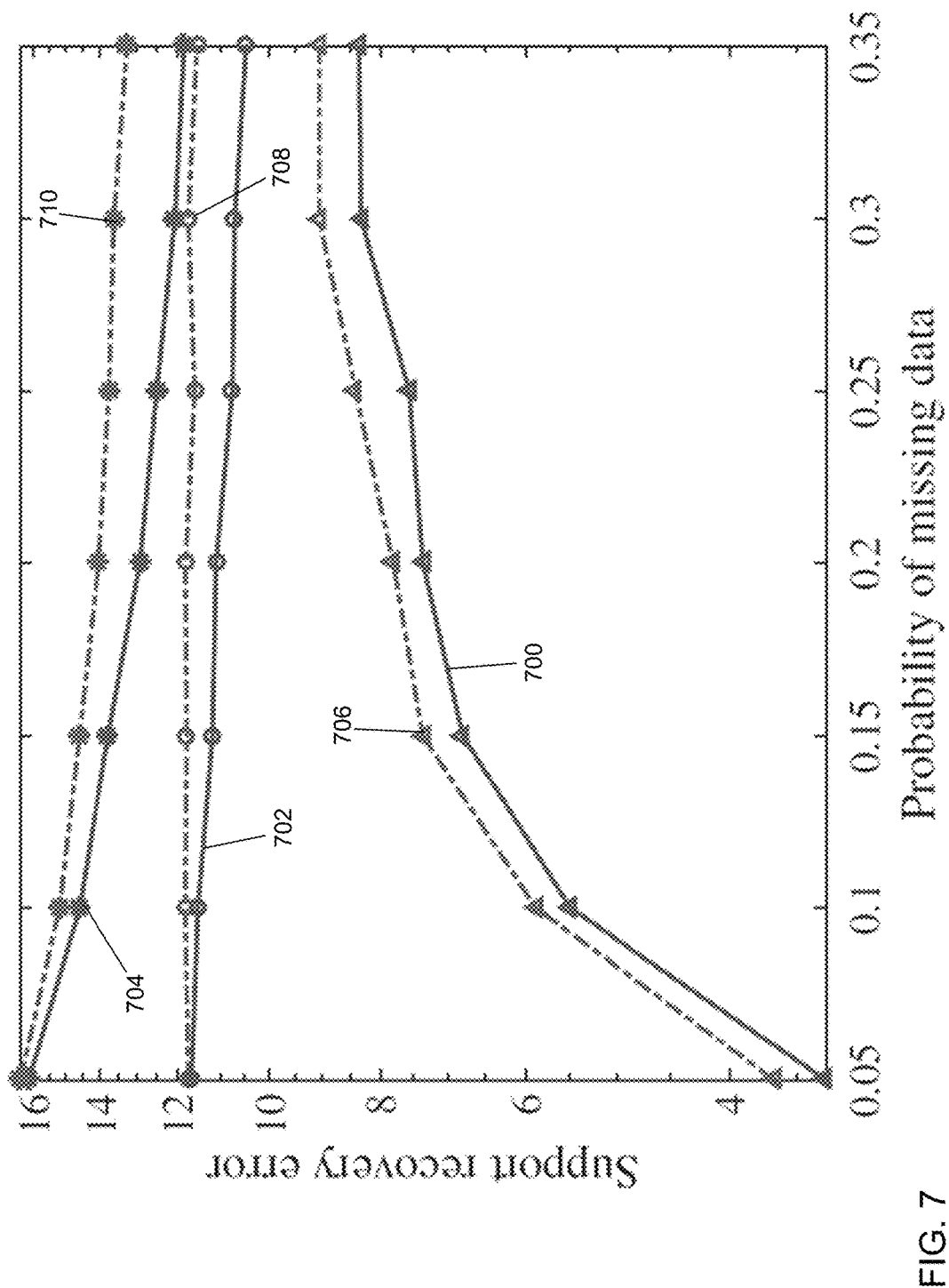
FIG. 7 shows a support recovery error as a function of the percentage of missing data in accordance with an illustrative embodiment.

Referring to FIG. 7, a support recovery error (SRE) is shown as a function of the probability of missing data $p_i$. The SRE is computed by finding locations of zeros and non-zeros in the true weight matrix W, comparing the locations with those from the estimate weight matrix $\hat{W}$, and counting how many are different. A first SRE curve 700 (solid line with triangles) shows the SRE of $\hat{W}$ computed using R-LGR with $r=0.9\|W\|_1$. A second SRE curve 702 (solid line with circles) shows the SRE of $\hat{W}$ computed using R-LGR with $r=\|W\|_1$. A third SRE curve 704 (solid line with asterisks) shows the SRE of $\hat{W}$ computed using R-LGR with $r=1.1\|W\|_1$. A fourth SRE curve 706 (dashed line with triangles) shows the SRE of $\hat{W}$ computed using LGR with $r=0.9\|W\|_1$. A fifth SRE curve 708 (dashed line with circles) shows the SRE of $\hat{W}$ computed using LGR with $r=\|W\|_1$. A sixth SRE curve 710 (dashed line with asterisks) shows the SRE of W computed using LGR with $r=1.1\|W\|_1$. R-LGR outperforms LGR for all three r levels, which suggests that R-LGR is more accurate in variable selection and support recovery. In applications like medical analysis where knowledge of which variable is more important than the others is important, R-LGR is advantageous due to its better accuracy in support recovery. Also note that both R-LGR and LGR performs better when r is set to be smaller than the actual l1-norm $\|W\|_1$. This may be because underestimating the radius promotes sparsity in $\hat{W}$, which benefits the support recovery.

In a second experiment, R-LGR, LGR, and MF-LGR were executed with 20 Newsgroup datasets as the plurality of training datasets 124. A subset of the complete dataset was used where two cross-domain datasets (Recreation vs. Talk, and Computer vs. Science) were used as two tasks. For each task, the objective was to learn a linear model to predict each news article's label. The first task had 1875 observations with 2000 variables, and the second task had 1827 observations with the 2000 variables. The missing data was artificially added into the observations as zeros, and the probability of missing data $p_i$ was varied between 5% and 30%. The dataset was randomly partitioned into training (70% of data) and validation (30% of data) datasets to assess a prediction accuracy of the learned models. The two tasks were assumed to be related with a graph structure having task 1 feed into task 2.

Table 1 below shows the support recovery error of R-LGR, LGR, and MF-LGR.

TABLE 1

| $p_i$ | R-LGR | LGR | MF-LGR |
|---|---|---|---|
| 0.05 | 382 | 394 | 221 |
| 0.10 | 376 | 403 | 1910 |
| 0.25 | 340 | 386 | 1930 |
| 0.20 | 361 | 419 | 1930 |
| 0.25 | 352 | 407 | 1930 |
| 0.30 | 331 | 426 | 1960 |

Since the real model W is unknown, an estimated ground-truth $W_i^*$ was generated for each task using ridge-regression without missing data. The support recovery error was computed by comparing the top 50% support of $W^*$ in magnitude and the top 50% support of $\hat{W}$ in magnitude for the three algorithms. The lowest error for each was provided using R-LGR. Therefore, R-LGR outperforms LGR and MF-LGR for all of the values of $p_i$ consistent with the results from the first experiment for SRE.

Table 2 below shows a label prediction error for R-LGR, LGR, and MF-LGR.

TABLE 2

| $p_i$ | R-LGR | LGR | MF-LGR |
|---|---|---|---|
| 0.05 | 97.2 | 92 | 164 |
| 0.10 | 82 | 84 | 671 |
| 0.25 | 10.1 | 104 | 741 |
| 0.20 | 10.8 | 114 | 774 |
| 0.25 | 122 | 124 | 833 |
| 0.30 | 130 | 130 | 1960953 |

Because $v_i > N_i$, a de-biasing step was added after computing $\hat{W}$, which improved the prediction accuracy for all three algorithms. Specifically, after computing estimators, a top 50% of the support of $\hat{W}$ with the highest magnitude was selected, and ridge regression was performed to compute $\overline{W}$ only on the selected support within each task. The labels were predicted by computing $\hat{y}_i = \text{sign}(X_i\overline{W}_i)$. As shown in Table 2, except for $p_i=0.05$, R-LGR yielded the smallest prediction error. The observations in this dataset were not low rank, which is why filling in the matrix using matrix factorization did not improve the performance of MF-LGR over LGR.

A fourth method referred to herein as M-LGR filled in missing values of the plurality of training datasets 124 using a computed mean value and estimated the weight matrix using standard LASSO with graph penalization. In a third experiment, a covariance estimation using each of R-LGR, LGR, MF-LGR, and M-LGR was compared with that computed without any missing data for $p_i=0.2$ and $p_i=0.4$ with landmine detection data, which is real data collected from 29 landmine fields that were treated as 29 tasks (See Ya Xue, et al., *Multi-Task Learning For Classification With Dirichlet Process Priors*, 8 Journal of Machine Learning Research, 35 (2007).

Each object in the data set was represented by a 9-dimensional feature vector and the corresponding binary label was one for a landmine and zero for clutter. The feature vectors were extracted from radar images, concatenating four moment-based features, three correlation-based features, one energy ratio feature, and one spatial variance feature. The landmine detection was modeled as a binary classification problem, where the goal was to provide an accurate prediction for the unlabeled feature vector. Classification of each dataset was considered a learning task. Missing values were introduced in the features matrix randomly with different probabilities. The results showed that R-LGR provided a better estimation of the covariance matrix with missing data compared to LGR, MF-LGR, and M-LGR.

Training application 122 handles missing data in multi-task learning using graph regularization to capture relatedness between connected tasks. To avoid bias and inaccurate inferences, training application 122 does not handle missing values separately from the modeling as done using imputation methods and matrix completion methods. Training application 122 handles the missing features within the learning process to provide improved results as demonstrated by the three experiments.

There are applications for training application 122 in areas such as object location and recognition in image processing, speech classification, data integration from different web directories, identification of handwritten digits, multiple microarray data integration in bioinformatics, prediction of disease progression, etc. where application of W determines a predicted value that the observation is associated with each label included in the plurality of training datasets 124. A label having the highest computed probability may be predicted and assigned to the observation in predicted dataset 426. When the target is a binary label, the value of the predicted value reflects how much the data is related to the label (which is related to the probability, but is un-normalized and not necessarily positive). The higher the prediction value is, the more likely the label applies to the data (in binary label case). However, the target variable may not be a binary label. It can also be a numerical value to predict, such as a blood pressure reading, a power usage, etc.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, using "and" or "or" in the detailed description is intended to include "and/or" unless specifically indicated otherwise.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated.

What is claimed is:

1. A non-transitory computer-readable medium having stored thereon computer-readable instructions that when executed by a computing device cause the computing device to:

for each of a plurality of related tasks,
compute an augmented observation matrix using an observation matrix and a predefined probability value that a value is missing in the observation matrix, wherein the observation matrix includes a plurality of observation vectors, wherein each observation vector includes a plurality of values, wherein each value of the plurality of values is associated with a variable to define a plurality of variables;
compute a plug-in autocovariance matrix using the computed augmented observation matrix and a noise value; and
compute a plug-in covariance vector using a target vector, the computed augmented observation matrix, and the noise value, wherein the target vector includes a target value associated with each of the plurality of observation vectors, wherein the target value is an indicator of a label of the associated observation vector;

compute a weight matrix used to predict the label for each of the plurality of variables and each of the plurality of related tasks;
(a) compute a gradient descent matrix using the computed plug-in autocovariance matrix, the computed plug-in covariance vector, the computed weight matrix, and a predefined relationship matrix, wherein the predefined relationship matrix defines a relationship between the plurality of related tasks, wherein the gradient descent matrix is computed using $\tilde{W}=\hat{W}^{t-1}-\eta(\bar{\nabla}+\lambda\hat{W}^{t-1}RR^T)$, where $\hat{W}^{t-1}$ is the computed weight matrix, where $\eta$ is a predefined step size, $\lambda$ is a predefined sparsity penalization weight value, R is the predefined relationship matrix, and $\bar{\nabla}=\Gamma_i\hat{W}_i^{t-1}-\gamma_i$ for i=1, ..., K, where K is a number of the of the plurality of related tasks, $\Gamma_i$ is the plug-in autocovariance matrix, and $\gamma_i$ is the plug-in covariance vector;
(b) compute an updated weight matrix using the computed gradient descent matrix;
repeat (a) and (b) with the computed updated weight matrix as the computed weight matrix until a convergence criterion is satisfied;
when the convergence criterion is satisfied, output the computed updated weight matrix;
read a new observation vector from a scoring dataset;
compute a probability value for each task of the plurality of related tasks using the computed updated weight matrix and the read new observation vector;
select a target value for the label of the read new observation vector based on a maximum computed probability value of the probability value computed for each task of the plurality of related tasks; and
output the selected target value to define the label for the read new observation vector that classifies the read new observation vector.

2. The non-transitory computer-readable medium of claim 1, wherein the predefined probability is a predefined probability vector with the predefined probability defined for each task of the plurality of related tasks.

3. The non-transitory computer-readable medium of claim 1, wherein the noise value is an independent random draw from a distribution function for each task of the plurality of related tasks.

4. The non-transitory computer-readable medium of claim 1, wherein a number of the plurality of variables is equal for each task of the plurality of related tasks.

5. The non-transitory computer-readable medium of claim 1, wherein a number of the plurality of observation vectors is different for at least one task of the plurality of related tasks.

6. The non-transitory computer-readable medium of claim 1, wherein possible values of the label are common to each task of the plurality of related tasks.

7. The non-transitory computer-readable medium of claim 1, wherein the predefined probability value is greater than zero and less than one.

8. The non-transitory computer-readable medium of claim 1, wherein the augmented observation matrix is computed using $$Z_i = \frac{1}{1-p_i} X_i,$$

where $p_i$ is the predefined probability value for a current task i of the plurality of related tasks, and $X_i$ is the observation matrix for the current task i.

9. The non-transitory computer-readable medium of claim 8, wherein the plug-in autocovariance matrix is computed using $$\Gamma_i = \frac{1}{\sigma_i} Z_i^T Z_i - \frac{p_i}{\sigma_i} \mathrm{diag}(Z_i),$$

where $\sigma_i$ is the noise value for the current task i.

10. The non-transitory computer-readable medium of claim 9, wherein the plug-in covariance vector is computed using $$\gamma_i = \frac{1}{\sigma_i} Z_i^T y_i,$$

where $y_i$ is the target vector for the current task i.

11. The non-transitory computer-readable medium of claim 1, wherein each variable of the plurality of variables describes a feature used to determine the label.

12. The non-transitory computer-readable medium of claim 1, wherein the updated weight matrix gradient descent is computed using a projected gradient descent method.

13. The non-transitory computer-readable medium of claim 1, wherein the updated weight matrix gradient descent is computed using an accelerated proximal gradient descent method.

14. The non-transitory computer-readable medium of claim 1, wherein the convergence criterion is a number of iterations of repeating (a) and (b).

15. The non-transitory computer-readable medium of claim 1, wherein the convergence criterion is computed based on a difference value computed between the updated weight matrix computed on a current iteration and a previous iteration of repeating (a) and (b).

16. The non-transitory computer-readable medium of claim 1, wherein the predefined relationship matrix R describes an undirected graph, where each task is a node, and a pair of tasks are connected if the pair of tasks are related.

17. The non-transitory computer-readable medium of claim 16, wherein the predefined relationship matrix R has dimension $R_{K,H}$, where H is a number of edges that connect pairs of tasks.

18. The non-transitory computer-readable medium of claim 17, wherein the predefined relationship matrix R is defined using $$R_{g,h} = \begin{cases} 1, & \text{if } g < k, \text{ and edge } h \text{ connects nodes } g, k, \\ -1, & \text{if } g > k, \text{ and edge } h \text{ connects nodes } g, k, \\ 0, & \text{otherwise.} \end{cases}$$

where g=1, 2, ..., K, k=1, 2, ..., K and h=1, 2, ..., N, where N is the number of edges.

19. The non-transitory computer-readable medium of claim 16, wherein the predefined relationship matrix R is computed by computing a statistical distribution for each task, computing a distance between the computed statistical distributions of each pair of tasks, and, when the distance between the pair of tasks is smaller than a predefined threshold distance, an edge is defined to connect the pair of tasks.

20. A computing device comprising:
a processor; and
a non-transitory computer-readable medium operably coupled to the processor, the computer-readable medium having computer-readable instructions stored thereon that, when executed by the processor, cause the computing device to
for each of a plurality of related tasks,
compute an augmented observation matrix using an observation matrix and a predefined probability value that a value is missing in the observation matrix, wherein the observation matrix includes a plurality of observation vectors, wherein each observation vector includes a plurality of values, wherein each value of the plurality of values is associated with a variable to define a plurality of variables;
compute a plug-in autocovariance matrix using the computed augmented observation matrix and a noise value; and
compute a plug-in covariance vector using a target vector, the computed augmented observation matrix, and the noise value, wherein the target vector includes a target value associated with each of the plurality of observation vectors, wherein the target value is an indicator of a label of the associated observation vector;
compute a weight matrix used to predict the characteristic label for each of the plurality of variables and each of the plurality of related tasks;
(a) compute a gradient descent matrix using the computed plug-in autocovariance matrix, the computed plug-in covariance vector, the computed weight matrix, and a predefined relationship matrix, wherein the predefined relationship matrix defines a relationship between the plurality of related tasks, wherein the gradient descent matrix is computed using $\tilde{W} = \hat{W}^{t-1} - \eta(\tilde{\nabla} + \lambda \hat{W}^{t-1} R R^T)$, where $\hat{W}^{t-1}$ is the computed weight matrix, where $\eta$ is a predefined step size, $\lambda$ is a predefined sparsity penalization weight value, R is the predefined relationship matrix, and $\tilde{\nabla} = \Gamma_i \hat{W}_i^{t-1} - \gamma_i$ for i=1, ..., K, where K is a number of the of the plurality of related tasks, $\Gamma_i$ is the plug-in autocovariance matrix, and $\gamma_i$ is the plug-in covariance vector;

(b) compute an updated weight matrix using the computed gradient descent matrix;

repeat (a) and (b) with the computed updated weight matrix as the computed weight matrix until a convergence criterion is satisfied;

when the convergence criterion is satisfied, output the computed updated weight matrix;

read a new observation vector from a scoring dataset;

compute a probability value for each task of the plurality of related tasks using the computed updated weight matrix and the read new observation vector;

select a target value for the label of the read new observation vector based on a maximum computed probability value of the probability value computed for each task of the plurality of related tasks; and output the selected target value to define the label for the read new observation vector that classifies the read new observation vector.

21. The computing device of claim 20, wherein the updated weight matrix gradient descent is computed using a projected gradient descent method.

22. The computing device of claim 20, wherein the updated weight matrix gradient descent is computed using an accelerated proximal gradient descent method.

23. The computing device of claim 20, wherein the augmented observation matrix is computed using $$Z_i = \frac{1}{1-p_i} X_i,$$

where $p_i$ is the predefined probability value for a current task i of the plurality of related tasks, and $X_i$ is the observation matrix for the current task i.

24. A method of computing an updated weight matrix used to predict a value for a label in a scoring dataset, the method comprising:

for each of a plurality of related tasks,
  compute, by a computing device, an augmented observation matrix using an observation matrix and a predefined probability value that a value is missing in the observation matrix, wherein the observation matrix includes a plurality of observation vectors, wherein each observation vector includes a plurality of values, wherein each value of the plurality of values is associated with a variable to define a plurality of variables;
  compute, by the computing device, a plug-in autocovariance matrix using the computed augmented observation matrix and a noise value; and
  compute, by the computing device, a plug-in covariance vector using a target vector, the computed augmented observation matrix, and the noise value, wherein the target vector includes a target value associated with each of the plurality of observation vectors, wherein the target value is an indicator of a label of the associated observation vector;

compute, by the computing device, a weight matrix used to predict the label for each of the plurality of variables and each of the plurality of related tasks;

(a) compute, by the computing device, a gradient descent matrix using the computed plug-in autocovariance matrix, the computed plug-in covariance vector, the computed weight matrix, and a predefined relationship matrix, wherein the predefined relationship matrix defines a relationship between the plurality of related tasks, wherein the gradient descent matrix is computed using $\tilde{W} = \hat{W}^{t-1} - \eta(\tilde{\nabla} + \lambda \hat{W}^{t-1} RR^T)$, where $\hat{W}^{t-1}$ is the computed weight matrix, where $\eta$ is a predefined step size, $\lambda$ is a predefined sparsity penalization weight value, R is the predefined relationship matrix, and $\tilde{\nabla} = \Gamma_i \hat{W}_i^{t-1} - \gamma_i$ for i=1, . . . , K, where K is a number of the of the plurality of related tasks, $\Gamma_i$ is the plug-in autocovariance matrix, and $\gamma_i$ is the plug-in covariance vector;

(b) compute, by the computing device, an updated weight matrix using the computed gradient descent matrix;

repeat, by the computing device, (a) and (b) with the computed updated weight matrix as the computed weight matrix until a convergence criterion is satisfied;

when the convergence criterion is satisfied, output, by the computing device, the computed updated weight matrix;

read, by the computing device, a new observation vector from a scoring dataset;

compute, by the computing device, a probability value for each task of the plurality of related tasks using the computed updated weight matrix and the read new observation vector;

select, by the computing device, a target value for the label of the read new observation vector based on a maximum computed probability value of the probability value computed for each task of the plurality of related tasks; and output, by the computing device, the selected target value to define the label for the read new observation vector that classifies the read new observation vector.

25. The method of claim 24, wherein each variable of the plurality of variables describes a feature used to determine the label.

26. The method of claim 24, wherein the updated weight matrix gradient descent is computed using a projected gradient descent method.

27. The method of claim 24, wherein the updated weight matrix gradient descent is computed using an accelerated proximal gradient descent method.

28. The method of claim 24, wherein the augmented observation matrix is computed using $$Z_i = \frac{1}{1-p_i} X_i,$$

where $p_i$ is the predefined probability value for a current task i of the plurality of related tasks, and $X_i$ is the observation matrix for the current task i.

29. The method of claim 28, wherein the plug-in autocovariance matrix is computed using $$\Gamma_i = \frac{1}{\sigma_i} Z_i^T Z_i - \frac{p_i}{\sigma_i} \text{diag}(Z_i),$$

where $\sigma_i$ is the noise value for the current task i.

30. The method of claim 29, wherein the plug-in covariance vector is computed using $$\gamma_i = \frac{1}{\sigma_i} Z_i^T y_i,$$

where $y_i$ is the target vector for the current task i.

* * * * *

UNITED STATES PATENT AND TRADEMARK OFFICE
CERTIFICATE OF CORRECTION

PATENT NO. : 10,402,741 B2
APPLICATION NO. : 15/833641
DATED : September 3, 2019
INVENTOR(S) : Xin Jiang Hunt et al.

Page 1 of 1

It is certified that error appears in the above-identified patent and that said Letters Patent is hereby corrected as shown below:

In the Specification

Column 6, Line 17:
Delete the phrase "where 1 = 1," and replace with --where $l$ = 1,--.

Column 6, Line 22:
Delete the phrase "variable value $y_{i,j}$," and replace with --variable value $y_{i,j}$,--.

Column 14, Line 65:
Delete the phrase "$cv = \|\widehat{W}^t - \widehat{W}^{t-1}\|_F^{\ 2}$" and replace with --$cv = \|\widehat{W}^t - \widehat{W}^{t-1}\|_F^2$--.

Column 19, Line 15:
Delete the phrase "$\|\widehat{W} - W\|_2^{\ 2}/\|W\|_2^{\ 2}$," and replace with --$\|\widehat{W} - W\|_2^2/\|W\|_2^2$--.

Column 20, Line 23:
Delete the phrase "$W_t$ * was generated" and replace with --$W_i^*$ was generated--.

In the Claims

Claim 20, Column 24, Lines 53-54:
Delete the phrase "used to predict the characteristic label" and replace with --used to predict the label--.

Signed and Sealed this
Third Day of December, 2019

Andrei Iancu
*Director of the United States Patent and Trademark Office*